(12) United States Patent
O'Brien

(10) Patent No.: US 6,942,978 B1
(45) Date of Patent: Sep. 13, 2005

US006942978B1

(54) TRANSMEMBRANE SERINE PROTEASE OVEREXPRESSED IN OVARIAN CARCINOMA AND USES THEREOF

(75) Inventor: Timothy J. O'Brien, Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 596 days.

(21) Appl. No.: 09/650,371

(22) Filed: Aug. 28, 2000

Related U.S. Application Data

(60) Division of application No. 09/518,046, filed on Mar. 2, 2000, now Pat. No. 6,294,663, which is a continuation-in-part of application No. 09/261,416, filed on Mar. 3, 1999, now Pat. No. 6,291,663.

(51) Int. Cl.[7] ............. G01N 33/53; G01N 33/536; G01N 33/537; G01N 33/48; G01N 33/50

(52) U.S. Cl. ............. 435/7.1; 435/7.2; 435/7.23; 435/7.4; 435/7.94; 436/64; 436/501; 436/503

(58) Field of Search ............. 436/64, 813, 501, 436/503; 435/7.1, 7.2, 7.23, 7.4, 7.94

(56) References Cited

U.S. PATENT DOCUMENTS 6,294,344 B1 * 9/2001 O'Brien

FOREIGN PATENT DOCUMENTS

WO   WO 98/41656   * 9/1998

OTHER PUBLICATIONS

Stenman et al, Biological Chemistry Hoppe–Seyler, 1998, vol. 369, Suppl. pp. 9–14 (abstract).*

* cited by examiner

*Primary Examiner*—Anthony C. Caputa
*Assistant Examiner*—Karen A. Canella
(74) *Attorney, Agent, or Firm*—Benjamin Aaron Adler

(57) ABSTRACT

The present invention provides a TADG-12 protein and a DNA fragment encoding such protein. Also provided is a vector/host cell capable of expressing the DNA. The present invention further provides various methods of early detection of associated ovarian and other malignancies, and of interactive therapies for cancer treatment utilizing the DNA and/or protein disclosed herein.

7 Claims, 12 Drawing Sheets

TADG12

```
1   TGGGTGGTGACGGGGCGGGGCACTGTGTTTATGACTTGTACCTCCCCAAGTCATGGACCATC
    W  V  V  T  A  A (H) C  V  Y  D  L  Y  L  P  K  S  W  T  I

61  CAGGTGGGTCTAGTTCCCTGTTGGACAATCCAGCCCCATCCCACTTGGTGGAGAAGATT
    Q  V  G  L  V  S  L  L  D  N  P  A  P  S  H  L  V  E  K  I
                                                    (SEQ ID NO. 5)

121 GTCTACCACAGCAAGTACAAGCCAAAGAGGCTGGGCAACGACATCGCCCTCCTA
    V  Y  H  S  K  Y  K  P  K  R  L  G  N  D  I  A  L  L
                                                    (SEQ ID NO. 6)
```

TADG12-V

```
1   GGGGTGGTGACGGCGGCGCACTGTGTTTATGAGATTGTAGCTCCTAGAGAAAGGGCAGACA
    G  V  V  T  A  A  H  C  V  Y  E  I  V  A  P  R  E  R  A  D  R

61  GAAGAGGAAGGAAGCTCCTGTGCTGGAGGAAAACCCACAAAAATGAAAGGACCTAGACCTT
    R  G  R  K  L  L  C  W  R  K  P  T  K  M  K  G  P  R  P  S

121 CCCATAGCTAATTCCAGTGGACCATGTTATGGCAGATACAGGCTTGTACCTCCCCAAGTC
    H  S  *       (SEQ ID NO. 8)

181 ATGGACCATCCAGGTGGGTCTAGTTTCCCTGTTGGACAATCCAGCCCCATCCCACTTGGT

241 GGAGAAGATTGTCTACCACAGCAAGTACAAGCCAAAGAGGCTGGGCAACGACATCGCCCT

301 CCTAATCACTAGTGCGGCCCTGCAGG    (SEQ ID NO. 7)
```

Fig. 1B

```
  1 CGGGAAAGGGCTGTGTTTATGGGAAGCCAGTAACACTGTGGCCTACTATCTCTTCCGTGG
 61 TGCCATCTACATTTTTGGGACTAGGAATTATGAGGTAGAGGTGGAGGCGGAGCCGGATG
121 TCAGAGGTCCTGAAATAGTCACCATGGGGAAAATGATCCGCCTGCTGTTGAAGCCCCCT
                       M   G   E   N   D   P   P   A   V   E   A   P   F        13
181 TCTCATTCCGATCGCTTTTGGCCTTGATGATTGAAAATAAGTCCTGTTGCACCAGATG
      S   F   R   S   L   E   G   L   D   D   L   K   I   S   P   V   A   P   D   A        33
241 CAGATGCTGTTGCTGCACAGATCCTGTCACTGCTGCCATTTGAAGTTTTTCCCAATCAT
      D   A   V   A   A   Q   I   L   S   L   L   P   F   E   V   F   S   Q   S   S        53
301 CGTCATTGGGGATCATTGATATTAGCACTGGTCTGGGCATCCACTTCG
      S   L   G   I   I   A   L   I   L   A   L   A   I   G   L   L   G   I   H   F   D    73
361 ACTGCTCAGGGAAGTACAGATGTCGCTCATCCTTTAAGTGTATCGAGCTGATAACTCGAT
      C   S   G   K   Y   R   C   R   S   S   F   K   C   I   E   L   I   T   R   C        93
421 GTGACGGAGTCTCGGATTGCAAAGACGGAGGACGAGTACCGCTGTGTCCGGGTGGGGTG
      D   G   V   S   D   C   K   D   G   E   D   E   Y   R   C   V   R   V   G   G       113
481 GTCAGAATGCCGTGTTCCAGGTGTTCACAGCTGCTTCGTGGAAGACCATGTGCTCCGATG
      Q   N   A   V   L   Q   V   F   T   A   A   S   W   K   T   M   C   S   D   D       133
541 ACTGGAAGGGTCACTACGCAAATGTTGCCTGTGCCCAACTGGGGTTTCCCAAGCTATGTGA
      W   K   G   H   Y   A   N   V   A   C   A   Q   L   G   F   P   S   Y   V   S       153
601 GTTCAGATAACCTCAGAGCTCGAGTCAGTTCGCTGGAGGGCCAGTTCCGGGAGGAGTTTGTGTCCA
      S   D   N   L   R   V   S   S   L   E   G   Q   F   R   E   E   F   V   S   I       173
661 TCGATCACCTCTTGCCAGATGACAAGGTGACTGCATTACACCACTCCAGTATATGTGAGGG
      D   H   L   L   P   D   D   K   V   T   A   L   H   H   S   V   Y   V   R   E       193
721 AGGGATGTGCCTCTGGCCACGTGGTTACCTTGCAGTGCACAGCCTGTGGTCATAGAAGGG
      G   C   A   S   G   H   V   V   T   L   Q   C   T   A   C   G   H   R   R   G       213
```

Fig. 4A

```
 781 GCTACAGCTCACGCATCGTGGGTGGAAACATGTCCTTGCTCTCGCAGTGGCCCTGGCAGG       233
      A  T  A  H  R  I  V  G  G  N  M  S  L  L  S  Q  W  P  W  Q  A
                  Y  S  S  R  I  V  G  G  N  M  S  L  L  S  Q  W  P  W  Q  A
 841 CCAGCCTTCAGTTCCAGGGCTACCACTGTGCGGGGCTCTGTCATCACGCCCCTGTGGA         253
      S  L  Q  F  Q  G  Y  H  L  C  G  G  S  V  I  T  P  L  W  I
 901 TCATCACTGCTGCACACTGTGTTTATGACTTGTACCTCCCCAAGTCATGGACCATCCAGG       273
      I  T  A  (A) H  C  V  Y  D  L  Y  L  P  K  S  Q  T  I  Q  V
 961 TGGGTCTAGTTTCCCTTGGACAATCCAGCCCCATCCACTTGGTGGAGAAGATTGTCT          293
      G  L  V  S  L  L  D  N  P  A  P  S  H  L  V  E  K  I  V  Y
1021 ACCACAGCAAGTACAAGCCAAAGAGGCTGGGCAATGACATCGCCCTTATGAAGCTGGCCG       313
      H  S  K  Y  K  P  K  R  L  G  (N) D  I  A  L  M  K  L  A  G
1081 GGCCACTCACGTTCAATGAAATGATCCAGCCTGTGTGCCTGCCCAACTCTGAAGAGAACT       333
      P  L  T  F  N  E  M  I  Q  P  V  C  L  P  N  S  E  E  N  F
1141 TCCCCGATGGGAAAGTGTGCTGGACGTCAGGAGGATGGAGCCACAGAGGATGGAGGTGACG     353
      P  D  G  K  V  C  W  T  S  G  A  T  E  D  G  G  D  A
1201 CCTCCCCTGTCCTGAACCACGGGCCGTCCCTTTGATTTCCAACAAGATCTGCAACCACA        373
      S  P  V  L  N  H  A  A  V  P  L  I  S  N  K  I  C  N  H  R
1261 GGGACGTGTACGGTGGCATCATCTCCCCTCCCTGTGTCTGCGCGGGCTACCTGACGGGTG       393
      D  V  Y  G  G  I  I  S  P  S  M  L  C  A  G  Y  L  T  G  G
1321 GCGTGGGACAGCTGCCAGGGGACAGCTGCCAGGGGAGCTTTGTCAAGAGAGGCTGT           413
      V  D  S  C  Q  G  (D) S  G  G  P  L  V  C  Q  E  R  R  L  W
1381 GGAAGTTAGTGGGAGGGCATCGGCTGCGCAGAGGTGAACAAGCCTGGGG                  433
      K  L  V  G  A  T  S  F  G  I  G  C  A  E  V  N  K  P  G  V
1441 TGTACACCCGTGTCACCTCCTTCCTGGACTGGATCCACGAGCAGATGGAGAGACCTAA         453
      Y  T  R  V  T  S  F  L  D  W  I  H  E  Q  M  E  R  D  L  K
1501 AAACCTGAAGAGGAAGGGACAAGTAGCCACCTGAGTTCCTGAGGTGATGAAGACAGCCC
      T  *           (SEQ ID NO. 2)
```

Fig. 4B

```
1561  GATCCTCCCCTGGACTCCCGTGTAGGAACCTGCACACGAGCAGACACCCTTGGAGCTCTG
1621  AGTTCCGGCACCAGTAGCGGGCCCGAAAGAGGCACCCTTCCATCTGATTCCAGCACAACC
1681  TTCAAGCTGCTTTTTGTTTTTGAGGTGGAGTCTCGCTCTGTTGCCCAGGCT
1741  GGAGTGCAGTGGCGAAATACCCGCTCACTGCTCAGCCTCCGCCTTCCCTGGTTCAAGCGATT
1801  CTCTTGCCTCAGCTTCCCCAGTAGCTGGGACCACAGGTGCCCGCCACCACCCAACTAA
1861  TTTTTGTATTTTTAGTAGAGACAGGGTTTCACCATGTTGGCCAGGCTGCTCTCAAACCCC
1921  TGACCTCAAATGATGTGCCTGCTTCAGCCTCCCACAGTGCTGGGATTACAGGCATGGGCC
1981  ACCACGCCTAGCCTCACGCCTCCTTTCTGATCTTCACTAAGACAAAGAAGCAGCAACTT
2041  GCAAGGGCGGCCCTTCCCACTGGTCCATCTGGTTTTCTCTCCAGGGTCTTGCAAAATTCC
2101  TGACGAGATAAGCAGTTATGTGACCTCACGTGCAGTCGCAGTGCACGTTTTCATCTTTAGGGACCAG
2161  ACGCACCAGCCCAGAAGTGCAGAACTGCAGTCACTGCACGTTTTCATCTTTAGGGACCAG
2221  AACCAAACCCACCCCTTTCTACTTTCCAAGACTTATTTTCACATGTGGGGAGGTTAATCTAG
2281  GAATGACTCGTTTAAGGCCTATTTCATGATTTCTTTGTAGCATTGGTGCTTGACGTAT
2341  TATTGTCCTTTGATTCCAAATAATATGTTTCCCTCAAAAAAAAAAAAAAAAAAAAA
2401  AAAAAAAAAAAA    (SEQ ID NO. 1)
```

Fig. 4C

```
Compc8    CEG..FVE  AQTGRCVNRR  LLCNGDNDCG  DQSDEAN.C   (SEQ ID NO: 9)
Matr      CPG.QFTC  .RTGRCIRKE  LRCDGWADCT  DHSDELN.C   (SEQ ID NO: 10)
Gp300-1   CQQGYFKC  QSEGQCIPSS  WVCDQDQDCD  DGSDERQDC   (SEQ ID NO: 11)
Gp300-2   CSSHQITC  .SNGQCIPSE  YRDDHVRDCP  DGADE.NDC   (SEQ ID NO: 12)
TADG12    CSGK.YRC  RSSFKCIELI  TRCDGVSDCK  DGEDEYR.C   (SEQ ID NO: 13)
Tmprss2   CSNSGIEC  DSSGTCINPS  NWCDGVSHCP  GGEDENR.C   (SEQ ID NO: 14)
Cons      C         C           C           C       C          DE    C
```

Fig. 5A

```
BovEntk   VRLVGGSGPH  EGRVEI.FHE  GQWGTVCDDR  WELRGGLVVC  RSLGYKGVQS
MacSR     VRLVGGSGPH  EGRVEI.LHS  GQWGTICDDR  WEVRVGQVVC  RSLGYPGVQA
TADG12    VRVGG...QN  AVLQVFTA..  ASWKTMCSDD  WKGHYANVAC  AQLGFT.SYV
Tmprss2   VRLYG...PN  FILQMYSSQR  KSWHPVCQDD  WNENYGRAAC  RDMGYKNNFY
HumEntk   VRFFNGTTNN  NGLVRFRIQ.  SIWHTACAEN  WTTGISNDVC  QLLGLGSG..
Cons      VR                                  W    C                C BovEntk   VHKRAYFGKG  TGPIWLNEVF  CFGK..ESSI  EECRIRQWGV  R.ACSHDEDA
MacSR     VHKAAHFGQG  TGPIWLNEVF  CFGR..ESSI  EECKIRQWGT  R.ACSHSEDA
TADG12    SSDNLRVSSL  EGQFREEFVS  I.DHLLPDDK  VTALHHSVYV  REGCASGHVV
Tmprss2   SSQGIVDDSG  STSFMKLNTS  A.GNV...DI  YKKLYHS...  .DACSSKAVV
HumEntk   NSSKPIFSTD  GGPFVKLNTA  PDGHLILTPS  Q.........  ...CLQDSLI
Cons                                                                  C BovEntk   GVTCT      (SEQ ID NO: 15)
MacSR     GVTCT      (SEQ ID NO: 16)
TADG12    TLQCT      (SEQ ID NO: 17)
Tmprss2   SLRCL      (SEQ ID NO: 18)
HumEntk   RLQC.      (SEQ ID NO: 19)
Cons         C
```

Fig. 5B

```
ProM      LWVLTAAHCK ......KPNL QVFLGKHNLR QRESSQEQSS VVRAVIHPDY
Try1      QWVVSAGHCY ......KSRI QVRLGEHNIE VLEGNEQFIN AAKIIRHPQY
Ka1       QWVLTAAHCF D.GLPLQDVW RIYSGILNLS DITKDTPFWQ IKEIIIHQNY
TADG12    LWIITAAHCV .YDLYLPKSW TIQVGLV..S LLDNPAPSHL VEKIVYHSKY
Tmprss2   EWIVTAAHCV IKPLNNPWHW TAFAGILRQS FMFYGA.GYQ VQKVISHPNY
Heps      DWVLTAAHCF PERNRVLSRW RVFAGAVAQA SPHGLQLG.. VQAVVYHGGY
Cons         W  A HC              G                         H  Y ProM      ......DAAS HDQDIMLLRL ARPAKLSELI QPLPLERDCS ANT..TSCHI
Try1      ......DRKT LNNDIMLIKL SSRAVINARV STISLPTAPP ATG..TKCLI
Ka1       ......KVSE GNHDIALIKL QAPLNYTEFQ KPICLPSKGD TSTIYTNCWV
TADG12    ......KPKR LGNDIALMKL AGPLTFNEMI QPVCLPNSEE NFPDGKVCWT
Tmprss2   ......DSKT KNNDIALMKL QKPLTFNDLV KPVCLPNPGM MLQPEQLCWI
Heps      LPFRDPNSEE NSNDIALVHL SSPLPLTEYI QPVCLPAAGQ ALVDGKICTV
Cons                 DI L  L                    L             C ProM      LGWGKTAD.. GDFPDTIQCA YIHLVSREEC EHA..YPGQI TQNMLCAGDE
Try1      SGWGNTASSG ADYPDELQCL DAPVLSQAKC EAS..YPGKI TSNMFCVGFL
Ka1       TGWGTFKEK. GEIQNILQKV NIPLVTNEEC QKR.YQDYKI TQRMVCAGYK
TADG12    SGWGAT.EDG GDASPVLNHA AVPLISNKIC NHRDVYGGII SPSMLCAGYL
Tmprss2   SGWGAT.EEK GKTSEVLNAA KVLLIETQRC NSRYVYDNLI TPAMICAGFL
Heps      TGWGNT.QYY GQQAGVLQEA RVPIISNDVC NGADFYGNQI KPKMFCAGYP
Cons          GWG                         C             I    M C G ProM      KYGKDSCQGD SGGPLVC  (SEQ ID NO: 20)
Try1      EGGKDSCQGD SGGPVVC  (SEQ ID NO: 21)
Ka1       EGGKDACKGD SGGPLVC  (SEQ ID NO: 22)
TADG12    TGGVDSCQGD SGGPLVC  (SEQ ID NO: 23)
Tmprss2   QGNVDSCQGD SGGPLVT.  (SEQ ID NO: 24)
Heps      EGGIDACQGD SGGPFVC  (SEQ ID NO: 25)
Cons          D C GD SGGP V
```

Fig. 5C

SEQUENCE LISTING

<160> NUMBER OF SEQ ID NOS: 153

<210> SEQ ID NO 1
<211> LENGTH: 2413
<212> TYPE: DNA
<213> ORGANISM: Homo sapiens
<220> FEATURE:
<221> NAME/KEY: CDS
<223> OTHER INFORMATION: entire cDNA sequence of TADG-12 gene

<400> SEQUENCE: 1

| | | | | |
|---|---|---|---|---|
| cgggaaaggg | ctgtgtttat | gggaagccag | taacactgtg | gcctactatc | 50 |
| tcttccgtgg | tgccatctac | attttttggga | ctcgggaatt | atgaggtaga | 100 |
| ggtggaggcg | gagccggatg | tcagaggtcc | tgaaatagtc | accatggggg | 150 |
| aaaatgatcc | gcctgctgtt | gaagcccct | tctcattccg | atcgcttttt | 200 |
| ggccttgatg | atttgaaaat | aagtcctgtt | gcaccagatg | cagatgctgt | 250 |
| tgctgcacag | atcctgtcac | tgctgccatt | tgaagttttt | tcccaatcat | 300 |
| cgtcattggg | gatcattgca | ttgatattag | cactggccat | tggtctgggc | 350 |
| atccacttcg | actgctcagg | gaagtacaga | tgtcgctcat | cctttaagtg | 400 |
| tatcgagctg | ataactcgat | gtgacggagt | ctcggattgc | aaagacgggg | 450 |
| aggacgagta | ccgctgtgtc | cgggtgggtg | gtcagaatgc | cgtgctccag | 500 |
| gtgttcacag | ctgcttcgtg | gaagaccatg | tgctccgatg | actggaaggg | 550 |
| tcactacgca | aatgttgcct | gtgcccaact | gggtttccca | agctatgtga | 600 |
| gttcagataa | cctcagagtg | agctcgctgg | aggggcagtt | ccgggaggag | 650 |
| tttgtgtcca | tcgatcacct | cttgccagat | gacaaggtga | ctgcattaca | 700 |
| ccactcagta | tatgtgaggg | agggatgtgc | ctctggccac | gtggttacct | 750 |
| tgcagtgcac | agcctgtggt | catagaaggg | gctacagctc | acgcatcgtg | 800 |
| ggtgaaaaca | tgtccttgct | ctcgcagtgg | ccctggcagg | ccagccttca | 850 |
| gttccagggc | taccacctgt | gcgggggctc | tgtcatcacg | cccctgtgga | 900 |
| tcatcactgc | tgcacactgt | gtttatgact | tgtacctccc | caagtcatgg | 950 |
| accatccagg | tgggtctagt | ttccctgttg | gacaatccag | ccccatccca | 1000 |
| cttggtggag | aagattgtct | accacagcaa | gtacaagcca | agaggctggg | 1050 |
| gcaatgacat | cgcccttatg | aagctggccg | ggccactcac | gttcaatgaa | 1100 |
| atgatccagc | ctgtgtgcct | gcccaactct | gaagagaact | tccccgatgg | 1150 |
| aaaagtgtgc | tggacgtcag | gatgggggc | cacagaggat | ggaggtgacg | 1200 |
| cctccctgt | cctgaaccac | gcggccgtcc | ctttgatttc | caacaagatc | 1250 |
| tgcaaccaca | gggacgtgta | cggtggcatc | atctccccct | ccatgctctg | 1300 |
| cgcgggctac | ctgacgggtg | gcgtgaacag | ctgccagggg | gacagcgggg | 1350 |
| ggccctggt | gtgtcaagag | aggaggctgt | ggaagttagt | gggagcgacc | 1400 |
| agctttggca | tcggctgcgc | agaggtgaac | aagcctgggg | tgtacacccg | 1450 |
| tgtcacctcc | ttcctggact | ggatccacga | gcagatggag | agagacctaa | 1500 |
| aaacctgaag | aggaagggga | caagtagcca | cctgagttcc | tgaggtgatg | 1550 |
| aagacagccc | gatcctcccc | tggactcccg | tgtaggaacc | tgcacacgag | 1600 |

-continued

| | |
|---|---|
| cagacaccct tggagctctg agttccggca ccagtagcgg gcccgaaaga | 1650 |
| ggcacccttc catctgattc cagcacaacc ttcaagctgc tttttgtttt | 1700 |
| ttgttttttt gaggtggagt ctcgctctgt tgcccaggct ggagtgcagt | 1750 |
| ggcgaaatac cctgctcact gcagcctccg cttccctggt tcaagcgatt | 1800 |
| ctcttgcctc agcttcccca gtagctggga ccacaggtgc ccgccaccac | 1850 |
| acccaactaa ttttgtatt tttagtagag acagggtttc accatgttgg | 1900 |
| ccaggctgct ctcaaacccc tgacctcaaa tgatgtgcct gcttcagcct | 1950 |
| cccacagtgc tgggattaca ggcatgggcc accacgccta gcctcacgct | 2000 |
| cctttctgat cttcactaag aacaaaagaa gcagcaactt gcaagggcgg | 2050 |
| cctttcccac tggtccatct ggttttctct ccagggtctt gcaaaattcc | 2100 |
| tgacgagata agcagttatg tgacctcacg tgcaaagcca ccaacagcca | 2150 |
| ctcagaaaag acgcaccagc ccagaagtgc agaactgcag tcactgcacg | 2200 |
| ttttcatctt tagggaccag aaccaaaccc acccttccta cttccaagac | 2250 |
| ttattttcac atgtggggag gttaatctag gaatgactcg tttaaggcct | 2300 |
| attttcatga tttctttgta gcatttggtg cttgacgtat tattgtcctt | 2350 |
| tgattccaaa taatatgttt ccttccctca aaaaaaaaa aaaaaaaaaa | 2400 |
| aaaaaaaaaa aaa | 2413 |

```
<210> SEQ ID NO 2
<211> LENGTH: 454
<212> TYPE: PRT
<213> ORGANISM: Homo sapiens
<220> FEATURE:
<223> OTHER INFORMATION: complete amino acid sequence of TADG-12
      protein

<400> SEQUENCE: 2

Met Gly Glu Asn Asp Pro Pro Ala Val Glu Ala Pro Phe Ser Phe
              5                   10                  15

Arg Ser Leu Phe Gly Leu Asp Asp Leu Lys Ile Ser Pro Val Ala
             20                   25                  30

Pro Asp Ala Asp Ala Val Ala Ala Gln Ile Leu Ser Leu Leu Pro
             35                   40                  45

Phe Glu Val Phe Ser Gln Ser Ser Ser Leu Gly Ile Ile Ala Leu
             50                   55                  60

Ile Leu Ala Leu Ala Ile Gly Leu Gly Ile His Phe Asp Cys Ser
             65                   70                  75

Gly Lys Tyr Arg Cys Arg Ser Ser Phe Lys Cys Ile Glu Leu Ile
             80                   85                  90

Thr Arg Cys Asp Gly Val Ser Asp Cys Lys Asp Gly Glu Asp Glu
             95                  100                 105

Tyr Arg Cys Val Arg Val Gly Gly Gln Asn Ala Val Leu Gln Val
            110                  115                 120

Phe Thr Ala Ala Ser Trp Lys Thr Met Cys Ser Asp Asp Trp Lys
            125                  130                 135

Gly His Tyr Ala Asn Val Ala Cys Ala Gln Leu Gly Phe Pro Ser
            140                  145                 150

Tyr Val Ser Ser Asp Asn Leu Arg Val Ser Ser Leu Glu Gly Gln
            155                  160                 165

Phe Arg Glu Glu Phe Val Ser Ile Asp His Leu Leu Pro Asp Asp
```

-continued

|  |  | 170 |  |  | 175 |  |  | 180 |  |
| --- | --- | --- | --- | --- | --- | --- | --- | --- | --- |

Lys Val Thr Ala Leu His His Ser Val Tyr Val Arg Glu Gly Cys
                  185                      190                      195

Ala Ser Gly His Val Val Thr Leu Gln Cys Thr Ala Cys Gly His
                  200                      205                      210

Arg Arg Gly Tyr Ser Ser Arg Ile Val Gly Gly Asn Met Ser Leu
                  215                      220                      225

Leu Ser Gln Trp Pro Trp Gln Ala Ser Leu Gln Phe Gln Gly Tyr
                  230                      235                      240

His Leu Cys Gly Gly Ser Val Ile Thr Pro Leu Trp Ile Ile Thr
                  245                      250                      255

Ala Ala His Cys Val Tyr Asp Leu Tyr Leu Pro Lys Ser Trp Thr
                  260                      265                      270

Ile Gln Val Gly Leu Val Ser Leu Leu Asp Asn Pro Ala Pro Ser
                  275                      280                      285

His Leu Val Glu Lys Ile Val Tyr His Ser Lys Tyr Lys Pro Lys
                  290                      295                      300

Arg Leu Gly Asn Asp Ile Ala Leu Met Lys Leu Ala Gly Pro Leu
                  305                      310                      315

Thr Phe Asn Glu Met Ile Gln Pro Val Cys Leu Pro Asn Ser Glu
                  320                      325                      330

Glu Asn Phe Pro Asp Gly Lys Val Cys Trp Thr Ser Gly Trp Gly
                  335                      340                      345

Ala Thr Glu Asp Gly Gly Asp Ala Ser Pro Val Leu Asn His Ala
                  350                      355                      360

Ala Val Pro Leu Ile Ser Asn Lys Ile Cys Asn His Arg Asp Val
                  365                      370                      375

Tyr Gly Gly Ile Ile Ser Pro Ser Met Leu Cys Ala Gly Tyr Leu
                  380                      385                      390

Thr Gly Gly Val Asp Ser Cys Gln Gly Asp Ser Gly Gly Pro Leu
                  395                      400                      405

Val Cys Gln Glu Arg Arg Leu Trp Lys Leu Val Gly Ala Thr Ser
                  410                      415                      420

Phe Gly Ile Gly Cys Ala Glu Val Asn Lys Pro Gly Val Tyr Thr
                  425                      430                      435

Arg Val Thr Ser Phe Leu Asp Trp Ile His Glu Gln Met Glu Arg
                  440                      445                      450

Asp Leu Lys Thr

<210> SEQ ID NO 3
<211> LENGTH: 2544
<212> TYPE: DNA
<213> ORGANISM: Homo sapiens
<220> FEATURE:
<221> NAME/KEY: CDS
<223> OTHER INFORMATION: entire cDNA sequence of TADG-12 variant gene

<400> SEQUENCE: 3

| cgggaaaggg ctgtgtttat gggaagccag taacactgtg gcctactatc | 50 |
| --- | --- |
| tcttccgtgg tgccatctac attttggga ctcgggaatt atgaggtaga | 100 |
| ggtggaggcg gagccggatg tcagaggtcc tgaaatagtc accatggggg | 150 |
| aaaatgatcc gcctgctgtt gaagccccct tctcattccg atcgcttttt | 200 |
| ggccttgatg atttgaaaat aagtcctgtt gcaccagatg cagatgctgt | 250 |

-continued

| | |
|---|---|
| tgctgcacag atcctgtcac tgctgccatt tgaagttttt tcccaatcat | 300 |
| cgtcattggg gatcattgca ttgatattag cactggccat tggtctgggc | 350 |
| atccacttcg actgctcagg gaagtacaga tgtcgctcat cctttaagtg | 400 |
| tatcgagctg ataactcgat gtgacggagt ctcggattgc aaagacgggg | 450 |
| aggacgagta ccgctgtgtc cgggtgggtg gtcagaatgc cgtgctccag | 500 |
| gtgttcacag ctgcttcgtg gaagaccatg tgctccgatg actggaaggg | 550 |
| tcactacgca aatgttgcct gtgcccaact gggtttccca agctatgtaa | 600 |
| gttcagataa cctcagagtg agctcgctgg aggggcagtt ccgggaggag | 650 |
| tttgtgtcca tcgatcacct cttgccagat gacaaggtga ctgcattaca | 700 |
| ccactcagta tatgtgaggg agggatgtgc ctctggccac gtggttacct | 750 |
| tgcagtgcac agcctgtggt catagaaggg gctacagctc acgcatcgtg | 800 |
| ggtgaaaca tgtccttgct ctcgcagtgg ccctggcagg ccagccttca | 850 |
| gttccagggc taccacctgt gcgggggctc tgtcatcacg ccctgtgga | 900 |
| tcatcactgc tgcacactgt gtttatgaga ttgtagctcc tagagaaagg | 950 |
| gcagacagaa gaggaaggaa gctcctgtgc tggaggaaac ccacaaaaat | 1000 |
| gaaaggacct agaccttccc atagctaatt ccagtggacc atgttatggc | 1050 |
| agatacaggc ttgtacctcc ccaagtcatg gaccatccag gtgggtctag | 1100 |
| tttccctgtt ggacaatcca gccccatccc acttggtgga aagattgtc | 1150 |
| taccacagca agtacaagcc aaagaggctg ggcaatgaca tcgcccttat | 1200 |
| gaagctggcc gggccactca cgttcaatga aatgatccag cctgtgtgcc | 1250 |
| tgcccaactc tgaagagaac ttccccgatg aaaagtgtg ctggacgtca | 1300 |
| ggatgggggg ccacagagga tggaggtgac gcctcccctg tcctgaacca | 1350 |
| cgcggccgtc ccttttgattt ccaacaagat ctgcaaccac agggacgtgt | 1400 |
| acggtggcat catctcccc tccatgctct gcgcgggcta cctgacgggt | 1450 |
| ggcgtggaca gctgccaggg ggacagcggg gggcccctgg tgtgtcaaga | 1500 |
| gaggaggctg tggaagttag tgggagcgac cagctttggc atcggctgcg | 1550 |
| cagaggtgaa caagcctggg gtgtacaccc gtgtcacctc cttcctggac | 1600 |
| tggatccacg agcagatgga gagagaccta aaaacctgaa gaggaagggg | 1650 |
| acaagtagcc acctgagttc ctgaggtgat gaagacagcc cgatcctccc | 1700 |
| ctggactccc gtgtaggaac ctgcacacga gcagacaccc ttggagctct | 1750 |
| gagttccgga ccagtagcg ggcccgaaag aggcacccctt ccatctgatt | 1800 |
| ccagcacaac cttcaagctg cttttttgttt tttgttttt tgaggtggag | 1850 |
| tctcgctctg ttgcccaggc tggagtgcag tggcgaaata ccctgctcac | 1900 |
| tgcagcctcc gcttccctgg ttcaagcgat tctcttgcct cagcttcccc | 1950 |
| agtagctggg accacaggtg cccgccacca cacccaacta attttttgtat | 2000 |
| ttttagtaga cagggtttt caccatgttg gccaggctgc tctcaaaccc | 2050 |
| ctgacctcaa atgatgtgcc tgcttcagcc tcccacagtg ctgggattac | 2100 |
| aggcatgggc caccacgcct agcctcacgc tcctttctga tcttcactaa | 2150 |
| gaacaaaaga agcagcaact tgcaagggcg gccttcccca ctggtccatc | 2200 |
| tggttttctc tccagggtct tgcaaaattc ctgacgagat aagcagttat | 2250 |

```
gtgacctcac gtgcaaagcc accaacagcc actcagaaaa gacgcaccag         2300
cccagaagtg cagaactgca gtcactgcac gttttcatct ttagggacca         2350
gaaccaaacc caccctttct acttccaaga cttattttca catgtgggga         2400
ggttaatcta ggaatgactc gtttaaggcc tattttcatg atttctttgt         2450
agcatttggt gcttgacgta ttattgtcct ttgattccaa ataatatgtt         2500
tccttccctc aaaaaaaaaa aaaaaaaaaa aaaaaaaaaa aaaa               2544
```

<210> SEQ ID NO 4
<211> LENGTH: 294
<212> TYPE: PRT
<213> ORGANISM: Homo sapiens
<220> FEATURE:
<223> OTHER INFORMATION: complete amino acid sequence of TADG-12
      variant protein

<400> SEQUENCE: 4

```
Met Gly Glu Asn Asp Pro Pro Ala Val Glu Ala Pro Phe Ser Phe
              5                  10                  15

Arg Ser Leu Phe Gly Leu Asp Asp Leu Lys Ile Ser Pro Val Ala
             20                  25                  30

Pro Asp Ala Asp Ala Val Ala Ala Gln Ile Leu Ser Leu Leu Pro
             35                  40                  45

Phe Glu Val Phe Ser Gln Ser Ser Ser Leu Gly Ile Ile Ala Leu
             50                  55                  60

Ile Leu Ala Leu Ala Ile Gly Leu Gly Ile His Phe Asp Cys Ser
             65                  70                  75

Gly Lys Tyr Arg Cys Arg Ser Ser Phe Lys Cys Ile Glu Leu Ile
             80                  85                  90

Thr Arg Cys Asp Gly Val Ser Asp Cys Lys Asp Gly Glu Asp Glu
             95                 100                 105

Tyr Arg Cys Val Arg Val Gly Gly Gln Asn Ala Val Leu Gln Val
            110                 115                 120

Phe Thr Ala Ala Ser Trp Lys Thr Met Cys Ser Asp Asp Trp Lys
            125                 130                 135

Gly His Tyr Ala Asn Val Ala Cys Ala Gln Leu Gly Phe Pro Ser
            140                 145                 150

Tyr Val Ser Ser Asp Asn Leu Arg Val Ser Ser Leu Glu Gly Gln
            155                 160                 165

Phe Arg Glu Glu Phe Val Ser Ile Asp His Leu Leu Pro Asp Asp
            170                 175                 180

Lys Val Thr Ala Leu His His Ser Val Tyr Val Arg Glu Gly Cys
            185                 190                 195

Ala Ser Gly His Val Val Thr Leu Gln Cys Thr Ala Cys Gly His
            200                 205                 210

Arg Arg Gly Tyr Ser Ser Arg Ile Val Gly Gly Asn Met Ser Leu
            215                 220                 225

Leu Ser Gln Trp Pro Trp Gln Ala Ser Leu Gln Phe Gln Gly Tyr
            230                 235                 240

His Leu Cys Gly Gly Ser Val Ile Thr Pro Leu Trp Ile Ile Thr
            245                 250                 255

Ala Ala His Cys Val Tyr Glu Ile Val Ala Pro Arg Glu Arg Ala
            260                 265                 270

Asp Arg Arg Gly Arg Lys Leu Leu Cys Trp Arg Lys Pro Thr Lys
```

Met Lys Gly Pro Arg Pro Ser His Ser
            290

<210> SEQ ID NO 5
<211> LENGTH: 174
<212> TYPE: DNA
<213> ORGANISM: Artificial sequence
<220> FEATURE:
<223> OTHER INFORMATION: nucleotide sequence of the subclone containing
      the 180 bp band from the PCR product for TADG-12

<400> SEQUENCE: 5

```
tgggtggtga cggcggcgca ctgtgtttat gacttgtacc tccccaagtc          50
atggaccatc caggtgggtc tagtttccct gttggacaat ccagccccat         100
cccacttggt ggagaagatt gtctaccaca gcaagtacaa gccaaagagg         150
ctgggcaacg acatcgccct ccta                                     174
```

<210> SEQ ID NO 6
<211> LENGTH: 58
<212> TYPE: PRT
<213> ORGANISM: Artificial sequence
<220> FEATURE:
<223> OTHER INFORMATION: deduced amino acid sequence of the 180 bp band
      from the PCR product for TADG-12

<400> SEQUENCE: 6

Trp Val Val Thr Ala Ala His Cys Val Tyr Asp Leu Tyr Leu Pro
              5                  10                  15

Lys Ser Trp Thr Ile Gln Val Gly Leu Val Ser Leu Leu Asp Asn
         20                  25                  30

Pro Ala Pro Ser His Leu Val Glu Lys Ile Val Tyr His Ser Lys
         35                  40                  45

Tyr Lys Pro Lys Arg Leu Gly Asn Asp Ile Ala Leu Leu
         50                  55

<210> SEQ ID NO 7
<211> LENGTH: 328
<212> TYPE: DNA
<213> ORGANISM: Artificial sequence
<220> FEATURE:
<223> OTHER INFORMATION: nucleotide sequence of the subclone containing
      the 300 bp band from the PCR product for
      TADG-12 variant, which contains an additional
      insert of 133 bases

<400> SEQUENCE: 7

```
gggtggtgac ggcggcgcac tgtgtttatg agattgtagc tcctagagaa          50
agggcagaca gaagaggaag gaagctcctg tgctggagga aacccacaaa         100
aatgaaagga cctagacctt cccatagcta attccagtgg accatgttat         150
ggcagataca ggcttgtacc tccccaagtc atggaccatc caggtgggtc         200
tagtttccct gttggacaat ccagccccat cccacttggt ggagaagatt         250
gtctaccaca gcaagtacaa gccaaagagg ctgggcaacg acatcgccct         300
cctaatcact agtgcggccg cctgcagg                                 328
```

<210> SEQ ID NO 8
<211> LENGTH: 42
<212> TYPE: PRT
<213> ORGANISM: Artificial sequence

```
<220> FEATURE:
<223> OTHER INFORMATION: deduced amino acid sequence of the 300 bp band
      from the PCR product for TADG-12 variant, which is
      a truncated form of TADG-12

<400> SEQUENCE: 8

Val Val Thr Ala Ala His Cys Val Tyr Glu Ile Val Ala Pro Arg
                 5                  10                  15

Glu Arg Ala Asp Arg Arg Gly Arg Lys Leu Leu Cys Trp Arg Lys
                20                  25                  30

Pro Thr Lys Met Lys Gly Pro Arg Pro Ser His Ser
                35                  40

<210> SEQ ID NO 9
<211> LENGTH: 34
<212> TYPE: PRT
<213> ORGANISM: Homo sapiens
<220> FEATURE:
<221> NAME/KEY: DOMAIN
<223> OTHER INFORMATION: LDLR-A domain of the complement subunit C8
      (Compc8)

<400> SEQUENCE: 9

Cys Glu Gly Phe Val Cys Ala Gln Thr Gly Arg Cys Val Asn Arg
                 5                  10                  15

Arg Leu Leu Cys Asn Gly Asp Asn Asp Cys Gly Asp Gln Ser Asp
                20                  25                  30

Glu Ala Asn Cys

<210> SEQ ID NO 10
<211> LENGTH: 34
<212> TYPE: PRT
<213> ORGANISM: Homo sapiens
<220> FEATURE:
<221> NAME/KEY: DOMAIN
<223> OTHER INFORMATION: LDLR-A domain of the serine protease
      matriptase (Matr)

<400> SEQUENCE: 10

Cys Pro Gly Gln Phe Thr Cys Arg Thr Gly Arg Cys Ile Arg Lys
                 5                  10                  15

Glu Leu Arg Cys Asp Gly Trp Ala Asp Cys Thr Asp His Ser Asp
                20                  25                  30

Glu Leu Asn Cys

<210> SEQ ID NO 11
<211> LENGTH: 37
<212> TYPE: PRT
<213> ORGANISM: Homo sapiens
<220> FEATURE:
<221> NAME/KEY: DOMAIN
<223> OTHER INFORMATION: LDLR-A domain of the glycoprotein GP300
      (Gp300-1)

<400> SEQUENCE: 11

Cys Gln Gln Gly Tyr Phe Lys Cys Gln Ser Glu Gly Gln Cys Ile
                 5                  10                  15

Pro Ser Ser Trp Val Cys Asp Gln Asp Gln Asp Cys Asp Asp Gly
                20                  25                  30

Ser Asp Glu Arg Gln Asp Cys
                35

<210> SEQ ID NO 12
```

-continued

```
<211> LENGTH: 35
<212> TYPE: PRT
<213> ORGANISM: Homo sapiens
<220> FEATURE:
<221> NAME/KEY: DOMAIN
<223> OTHER INFORMATION: LDLR-A domain of the glycoprotein GP300
      (Gp300-2)

<400> SEQUENCE: 12

Cys Ser Ser His Gln Ile Thr Cys Ser Asn Gly Gln Cys Ile Pro
                5                  10                  15

Ser Glu Tyr Arg Cys Asp His Val Arg Asp Cys Pro Asp Gly Ala
            20                  25                  30

Asp Glu Asn Asp Cys
            35

<210> SEQ ID NO 13
<211> LENGTH: 35
<212> TYPE: PRT
<213> ORGANISM: Homo sapiens
<220> FEATURE:
<221> NAME/KEY: DOMAIN
<222> LOCATION: 74...108
<223> OTHER INFORMATION: LDLR-A domain of TADG-12

<400> SEQUENCE: 13

Cys Ser Gly Lys Tyr Arg Cys Arg Ser Ser Phe Lys Cys Ile Glu
                5                  10                  15

Leu Ile Thr Arg Cys Asp Gly Val Ser Asp Cys Lys Asp Gly Glu
            20                  25                  30

Asp Glu Tyr Arg Cys
            35

<210> SEQ ID NO 14
<211> LENGTH: 36
<212> TYPE: PRT
<213> ORGANISM: Homo sapiens
<220> FEATURE:
<221> NAME/KEY: DOMAIN
<223> OTHER INFORMATION: LDLR-A domain of the serine protease TMPRSS2
      Tmprss2

<400> SEQUENCE: 14

Cys Ser Asn Ser Gly Ile Glu Cys Asp Ser Ser Gly Thr Cys Ile
                5                  10                  15

Asn Pro Ser Asn Trp Cys Asp Gly Val Ser His Cys Pro Gly Gly
            20                  25                  30

Glu Asp Glu Asn Arg Cys
            35

<210> SEQ ID NO 15
<211> LENGTH: 101
<212> TYPE: PRT
<213> ORGANISM: Bos taurus
<220> FEATURE:
<221> NAME/KEY: DOMAIN
<223> OTHER INFORMATION: SRCR domain of bovine enterokinase (BovEntk)

<400> SEQUENCE: 15

Val Arg Leu Val Gly Gly Ser Gly Pro His Glu Gly Arg Val Glu
                5                  10                  15

Ile Phe His Glu Gly Gln Trp Gly Thr Val Cys Asp Asp Arg Trp
            20                  25                  30

Glu Leu Arg Gly Gly Leu Val Val Cys Arg Ser Leu Gly Tyr Lys
```

```
                        35                  40                  45
Gly Val Gln Ser Val His Lys Arg Ala Tyr Phe Gly Lys Gly Thr
                50                  55                  60

Gly Pro Ile Trp Leu Asn Glu Val Phe Cys Phe Gly Lys Glu Ser
                65                  70                  75

Ser Ile Glu Glu Cys Arg Ile Arg Gln Trp Gly Val Arg Ala Cys
                80                  85                  90

Ser His Asp Glu Asp Ala Gly Val Thr Cys Thr
                95                  100

<210> SEQ ID NO 16
<211> LENGTH: 101
<212> TYPE: PRT
<213> ORGANISM: Homo sapiens
<220> FEATURE:
<221> NAME/KEY: DOMAIN
<223> OTHER INFORMATION: SRCR domain of human macrophage scavenger
      receptor (MacSR)

<400> SEQUENCE: 16

Val Arg Leu Val Gly Gly Ser Gly Pro His Glu Gly Arg Val Glu
                 5                  10                  15

Ile Leu His Ser Gly Gln Trp Gly Thr Ile Cys Asp Asp Arg Trp
                20                  25                  30

Glu Val Arg Val Gly Gln Val Val Cys Arg Ser Leu Gly Tyr Pro
                35                  40                  45

Gly Val Gln Ala Val His Lys Ala Ala His Phe Gly Gln Gly Thr
                50                  55                  60

Gly Pro Ile Trp Leu Asn Glu Val Phe Cys Phe Gly Arg Glu Ser
                65                  70                  75

Ser Ile Glu Glu Cys Lys Ile Arg Gln Trp Gly Thr Arg Ala Cys
                80                  85                  90

Ser His Ser Glu Asp Ala Gly Val Thr Cys Thr
                95                  100

<210> SEQ ID NO 17
<211> LENGTH: 98
<212> TYPE: PRT
<213> ORGANISM: Homo sapiens
<220> FEATURE:
<221> NAME/KEY: DOMAIN
<222> LOCATION: 109...206
<223> OTHER INFORMATION: SRCR domain of TADG-12 (TADG12)

<400> SEQUENCE: 17

Val Arg Val Gly Gly Gln Asn Ala Val Leu Gln Val Phe Thr Ala
                 5                  10                  15

Ala Ser Trp Lys Thr Met Cys Ser Asp Asp Trp Lys Gly His Tyr
                20                  25                  30

Ala Asn Val Ala Cys Ala Gln Leu Gly Phe Pro Ser Tyr Val Ser
                35                  40                  45

Ser Asp Asn Leu Arg Val Ser Ser Leu Glu Gly Gln Phe Arg Glu
                50                  55                  60

Glu Phe Val Ser Ile Asp His Leu Leu Pro Asp Asp Lys Val Thr
                65                  70                  75

Ala Leu His His Ser Val Tyr Val Arg Glu Gly Cys Ala Ser Gly
                80                  85                  90

His Val Val Thr Leu Gln Cys Thr
                95
```

-continued

```
<210> SEQ ID NO 18
<211> LENGTH: 94
<212> TYPE: PRT
<213> ORGANISM: Homo sapiens
<220> FEATURE:
<221> NAME/KEY: DOMAIN
<223> OTHER INFORMATION: SRCR domain of the serine protease TMPRSS2
      (Tmprss2)

<400> SEQUENCE: 18

Val Arg Leu Tyr Gly Pro Asn Phe Ile Leu Gln Met Tyr Ser Ser
                 5                  10                  15

Gln Arg Lys Ser Trp His Pro Val Cys Gln Asp Asp Trp Asn Glu
             20                  25                  30

Asn Tyr Gly Arg Ala Ala Cys Arg Asp Met Gly Tyr Lys Asn Asn
             35                  40                  45

Phe Tyr Ser Ser Gln Gly Ile Val Asp Asp Ser Gly Ser Thr Ser
             50                  55                  60

Phe Met Lys Leu Asn Thr Ser Ala Gly Asn Val Asp Ile Tyr Lys
             65                  70                  75

Lys Leu Tyr His Ser Asp Ala Cys Ser Ser Lys Ala Val Val Ser
             80                  85                  90

Leu Arg Cys Leu

<210> SEQ ID NO 19
<211> LENGTH: 90
<212> TYPE: PRT
<213> ORGANISM: Homo sapiens
<220> FEATURE:
<221> NAME/KEY: DOMAIN
<223> OTHER INFORMATION: SRCR domain of human enterokinase (HumEntk)

<400> SEQUENCE: 19

Val Arg Phe Phe Asn Gly Thr Thr Asn Asn Gly Leu Val Arg
                 5                  10                  15

Phe Arg Ile Gln Ser Ile Trp His Thr Ala Cys Ala Glu Asn Trp
             20                  25                  30

Thr Thr Gln Ile Ser Asn Asp Val Cys Gln Leu Leu Gly Leu Gly
             35                  40                  45

Ser Gly Asn Ser Ser Lys Pro Ile Phe Ser Thr Asp Gly Gly Pro
             50                  55                  60

Phe Val Lys Leu Asn Thr Ala Pro Asp Gly His Leu Ile Leu Thr
             65                  70                  75

Pro Ser Gln Gln Cys Leu Gln Asp Ser Leu Ile Arg Leu Gln Cys
             80                  85                  90

<210> SEQ ID NO 20
<211> LENGTH: 149
<212> TYPE: PRT
<213> ORGANISM: Homo sapiens
<220> FEATURE:
<221> NAME/KEY: DOMAIN
<223> OTHER INFORMATION: protease domain of protease M (ProM)

<400> SEQUENCE: 20

Leu Trp Val Leu Thr Ala Ala His Cys Lys Lys Pro Asn Leu Gln
                 5                  10                  15

Val Phe Leu Gly Lys His Asn Leu Arg Gln Arg Glu Ser Ser Gln
             20                  25                  30
```

-continued

Glu Gln Ser Ser Val Val Arg Ala Val Ile His Pro Asp Tyr Asp
                35                  40                  45

Ala Ala Ser His Asp Gln Asp Ile Met Leu Leu Arg Leu Ala Arg
            50                  55                  60

Pro Ala Lys Leu Ser Glu Leu Ile Gln Pro Leu Pro Leu Glu Arg
        65                  70                  75

Asp Cys Ser Ala Asn Thr Thr Ser Cys His Ile Leu Gly Trp Gly
    80                  85                  90

Lys Thr Ala Asp Gly Asp Phe Pro Asp Thr Ile Gln Cys Ala Tyr
95                  100                 105

Ile His Leu Val Ser Arg Glu Glu Cys Glu His Ala Tyr Pro Gly
            110                 115                 120

Gln Ile Thr Gln Asn Met Leu Cys Ala Gly Asp Glu Lys Tyr Gly
        125                 130                 135

Lys Asp Ser Cys Gln Gly Asp Ser Gly Gly Pro Leu Val Cys
    140                 145

<210> SEQ ID NO 21
<211> LENGTH: 151
<212> TYPE: PRT
<213> ORGANISM: Homo sapiens
<220> FEATURE:
<221> NAME/KEY: DOMAIN
<223> OTHER INFORMATION: protease domain of trypsinogen I (Try1)

<400> SEQUENCE: 21

Gln Trp Val Val Ser Ala Gly His Cys Tyr Lys Ser Arg Ile Gln
                5                   10                  15

Val Arg Leu Gly Glu His Asn Ile Glu Val Leu Glu Gly Asn Glu
            20                  25                  30

Gln Phe Ile Asn Ala Ala Lys Ile Ile Arg His Pro Gln Tyr Asp
        35                  40                  45

Arg Lys Thr Leu Asn Asn Asp Ile Met Leu Ile Lys Leu Ser Ser
    50                  55                  60

Arg Ala Val Ile Asn Ala Arg Val Ser Thr Ile Ser Leu Pro Thr
65                  70                  75

Ala Pro Pro Ala Thr Gly Thr Lys Cys Leu Ile Ser Gly Trp Gly
            80                  85                  90

Asn Thr Ala Ser Ser Gly Ala Asp Tyr Pro Asp Glu Leu Gln Cys
        95                  100                 105

Leu Asp Ala Pro Val Leu Ser Gln Ala Lys Cys Glu Ala Ser Tyr
    110                 115                 120

Pro Gly Lys Ile Thr Ser Asn Met Phe Cys Val Gly Phe Leu Glu
125                 130                 135

Gly Gly Lys Asp Ser Cys Gln Gly Asp Ser Gly Gly Pro Val Val
            140                 145                 150

Cys

<210> SEQ ID NO 22
<211> LENGTH: 158
<212> TYPE: PRT
<213> ORGANISM: Homo sapiens
<220> FEATURE:
<221> NAME/KEY: DOMAIN
<223> OTHER INFORMATION: protease domain of plasma kallikrein (Kal)

<400> SEQUENCE: 22

Gln Trp Val Leu Thr Ala Ala His Cys Phe Asp Gly Leu Pro Leu

-continued

```
                5                   10                  15
Gln Asp Val Trp Arg Ile Tyr Ser Gly Ile Leu Asn Leu Ser Asp
            20                  25                  30

Ile Thr Lys Asp Thr Pro Phe Ser Gln Ile Lys Glu Ile Ile Ile
            35                  40                  45

His Gln Asn Tyr Lys Val Ser Glu Gly Asn His Asp Ile Ala Leu
            50                  55                  60

Ile Lys Leu Gln Ala Pro Leu Asn Tyr Thr Glu Phe Gln Lys Pro
            65                  70                  75

Ile Cys Leu Pro Ser Lys Gly Asp Thr Ser Thr Ile Tyr Thr Asn
            80                  85                  90

Cys Trp Val Thr Gly Trp Gly Phe Ser Lys Glu Lys Gly Glu Ile
            95                  100                 105

Gln Asn Ile Leu Gln Lys Val Asn Ile Pro Leu Val Thr Asn Glu
            110                 115                 120

Glu Cys Gln Lys Arg Tyr Gln Asp Tyr Lys Ile Thr Gln Arg Met
            125                 130                 135

Val Cys Ala Gly Tyr Lys Glu Gly Gly Lys Asp Ala Cys Lys Gly
            140                 145                 150

Asp Ser Gly Gly Pro Leu Val Cys
            155
```

<210> SEQ ID NO 23
<211> LENGTH: 157
<212> TYPE: PRT
<213> ORGANISM: Homo sapiens
<220> FEATURE:
<221> NAME/KEY: DOMAIN
<223> OTHER INFORMATION: protease domain of TADG-12 (TADG12)

<400> SEQUENCE: 23

```
Leu Trp Ile Ile Thr Ala Ala His Cys Val Tyr Asp Leu Tyr Leu
                5                   10                  15

Pro Lys Ser Trp Thr Ile Gln Val Gly Leu Val Ser Leu Leu Asp
            20                  25                  30

Asn Pro Ala Pro Ser His Leu Val Glu Lys Ile Val Tyr His Ser
            35                  40                  45

Lys Tyr Lys Pro Lys Arg Leu Gly Asn Asp Ile Ala Leu Met Lys
            50                  55                  60

Leu Ala Gly Pro Leu Thr Phe Asn Glu Met Ile Gln Pro Val Cys
            65                  70                  75

Leu Pro Asn Ser Glu Glu Asn Phe Pro Asp Gly Lys Val Cys Trp
            80                  85                  90

Thr Ser Gly Trp Gly Ala Thr Glu Asp Gly Gly Asp Ala Ser Pro
            95                  100                 105

Val Leu Asn His Ala Ala Val Pro Leu Ile Ser Asn Lys Ile Cys
            110                 115                 120

Asn His Arg Asp Val Tyr Gly Gly Ile Ile Ser Pro Ser Met Leu
            125                 130                 135

Cys Ala Gly Tyr Leu Thr Gly Gly Val Asp Ser Cys Gln Gly Asp
            140                 145                 150

Ser Gly Gly Pro Leu Val Cys
            155
```

<210> SEQ ID NO 24
<211> LENGTH: 159

```
<212> TYPE: PRT
<213> ORGANISM: Homo sapiens
<220> FEATURE:
<221> NAME/KEY: DOMAIN
<223> OTHER INFORMATION: protease domain of TMPRSS2 (Tmprss2)

<400> SEQUENCE: 24

Glu Trp Ile Val Thr Ala Ala His Cys Val Glu Lys Pro Leu Asn
            5                  10                  15

Asn Pro Trp His Trp Thr Ala Phe Ala Gly Ile Leu Arg Gln Ser
            20                  25                  30

Phe Met Phe Tyr Gly Ala Gly Tyr Gln Val Gln Lys Val Ile Ser
            35                  40                  45

His Pro Asn Tyr Asp Ser Lys Thr Lys Asn Asn Asp Ile Ala Leu
            50                  55                  60

Met Lys Leu Gln Lys Pro Leu Thr Phe Asn Asp Leu Val Lys Pro
            65                  70                  75

Val Cys Leu Pro Asn Pro Gly Met Met Leu Gln Pro Glu Gln Leu
            80                  85                  90

Cys Trp Ile Ser Gly Trp Gly Ala Thr Glu Glu Lys Gly Lys Thr
            95                 100                 105

Ser Glu Val Leu Asn Ala Ala Lys Val Leu Leu Ile Glu Thr Gln
           110                 115                 120

Arg Cys Asn Ser Arg Tyr Val Tyr Asp Asn Leu Ile Thr Pro Ala
           125                 130                 135

Met Ile Cys Ala Gly Phe Leu Gln Gly Asn Val Asp Ser Cys Gln
           140                 145                 150

Gly Asp Ser Gly Gly Pro Leu Val Thr
           155

<210> SEQ ID NO 25
<211> LENGTH: 164
<212> TYPE: PRT
<213> ORGANISM: Homo sapiens
<220> FEATURE:
<221> NAME/KEY: DOMAIN
<223> OTHER INFORMATION: protease domain of Hepsin (Heps)

<400> SEQUENCE: 25

Asp Trp Val Leu Thr Ala Ala His Cys Phe Pro Glu Arg Asn Arg
            5                  10                  15

Val Leu Ser Arg Trp Arg Val Phe Ala Gly Ala Val Ala Gln Ala
            20                  25                  30

Ser Pro His Gly Leu Gln Leu Gly Val Gln Ala Val Val Tyr His
            35                  40                  45

Gly Gly Tyr Leu Pro Phe Arg Asp Pro Asn Ser Glu Glu Asn Ser
            50                  55                  60

Asn Asp Ile Ala Leu Val His Leu Ser Ser Pro Leu Pro Leu Thr
            65                  70                  75

Glu Tyr Ile Gln Pro Val Cys Leu Pro Ala Ala Gly Gln Ala Leu
            80                  85                  90

Val Asp Gly Lys Ile Cys Thr Val Thr Gly Trp Gly Asn Thr Gln
            95                 100                 105

Tyr Tyr Gly Gln Gln Ala Gly Val Leu Gln Glu Ala Arg Val Pro
           110                 115                 120

Ile Ile Ser Asn Asp Val Cys Asn Gly Ala Asp Phe Tyr Gly Asn
           125                 130                 135
```

```
Gln Ile Lys Pro Lys Met Phe Cys Ala Gly Tyr Pro Glu Gly Gly
                140                 145                 150

Ile Asp Ala Cys Gln Gly Asp Ser Gly Gly Pro Phe Val Cys
                155                 160

<210> SEQ ID NO 26
<211> LENGTH: 23
<212> TYPE: DNA
<213> ORGANISM: Artificial sequence
<220> FEATURE:
<221> NAME/KEY: primer_bind
<222> LOCATION: 6, 9, 12, 15, 18
<223> OTHER INFORMATION: forward redundant primer for the consensus
      sequences of amino acids surrounding the catalytic
      triad for serine proteases, n = inosine

<400> SEQUENCE: 26
tgggtngtna cngcngcnca ytg                                           23

<210> SEQ ID NO 27
<211> LENGTH: 20
<212> TYPE: DNA
<213> ORGANISM: Artificial sequence
<220> FEATURE:
<221> NAME/KEY: primer_bind
<222> LOCATION: 3, 6, 9, 12, 15, 18
<223> OTHER INFORMATION: reverse redundant primer for the consensus
      sequences of amino acids surrounding the catalytic
      triad for serine proteases, n = inosine

<400> SEQUENCE: 27
arnarngcna tntcnttncc                                               20

<210> SEQ ID NO 28
<211> LENGTH: 20
<212> TYPE: DNA
<213> ORGANISM: Artificial sequence
<220> FEATURE:
<221> NAME/KEY: primer_bind
<223> OTHER INFORMATION: forward oligonucleotide primer for TADG-12
      used for quantitative PCR

<400> SEQUENCE: 28
gaaacatgtc cttgctctcg                                               20

<210> SEQ ID NO 29
<211> LENGTH: 20
<212> TYPE: DNA
<213> ORGANISM: Artificial sequence
<220> FEATURE:
<221> NAME/KEY: primer_bind
<223> OTHER INFORMATION: reverse oligonucleotide primer for TADG-12
      used for quantitative PCR

<400> SEQUENCE: 29
actaacttcc acagcctcct                                               20

<210> SEQ ID NO 30
<211> LENGTH: 20
<212> TYPE: DNA
<213> ORGANISM: Artificial sequence
<220> FEATURE:
<221> NAME/KEY: primer_bind
<223> OTHER INFORMATION: forward oligonucleotide primer for TADG-12
      variant (TADG-12V) used for quantitative PCR

<400> SEQUENCE: 30
tccaggtggg tctagtttcc                                               20
```

<210> SEQ ID NO 31
<211> LENGTH: 20
<212> TYPE: DNA
<213> ORGANISM: Artificial sequence
<220> FEATURE:
<221> NAME/KEY: primer_bind
<223> OTHER INFORMATION: reverse oligonucleotide primer for TADG-12
      variant (TADG-12V) used for quantitative PCR

<400> SEQUENCE: 31
ctctttggct tgtacttgct                                          20

<210> SEQ ID NO 32
<211> LENGTH: 20
<212> TYPE: DNA
<213> ORGANISM: Artificial sequence
<220> FEATURE:
<221> NAME/KEY: primer_bind
<223> OTHER INFORMATION: forward oligonucleotide primer for (-tubulin
      used as an internal control for quantitative PCR

<400> SEQUENCE: 32
cgcatcaacg tgtactacaa                                          20

<210> SEQ ID NO 33
<211> LENGTH: 20
<212> TYPE: DNA
<213> ORGANISM: Artificial sequence
<220> FEATURE:
<221> NAME/KEY: primer_bind
<223> OTHER INFORMATION: reverse oligonucleotide primer for (-tubulin
      used as an internal control for quantitative PCR

<400> SEQUENCE: 33
tacgagctgg tggactgaga                                          20

<210> SEQ ID NO 34
<211> LENGTH: 12
<212> TYPE: PRT
<213> ORGANISM: Artificial sequence
<220> FEATURE:
<223> OTHER INFORMATION: a poly-lysine linked multiple antigen peptide
      derived from the TADG-12 carboxy-terminal protein
      sequence, present in full length TADG-12, but not
      in TADG-12V

<400> SEQUENCE: 34

Trp Ile His Glu Gln Met Glu Arg Asp Leu Lys Thr
              5                  10

<210> SEQ ID NO 35
<211> LENGTH: 9
<212> TYPE: PRT
<213> ORGANISM: Homo sapiens
<220> FEATURE:
<222> LOCATION: 40...48
<223> OTHER INFORMATION: TADG-12 peptide

<400> SEQUENCE: 35

Ile Leu Ser Leu Leu Pro Phe Glu Val
              5

<210> SEQ ID NO 36
<211> LENGTH: 9
<212> TYPE: PRT
<213> ORGANISM: Homo sapiens
<220> FEATURE:

```
<222> LOCATION: 144...152
<223> OTHER INFORMATION: TADG-12 peptide

<400> SEQUENCE: 36

Ala Gln Leu Gly Phe Pro Ser Tyr Val
                5

<210> SEQ ID NO 37
<211> LENGTH: 9
<212> TYPE: PRT
<213> ORGANISM: Homo sapiens
<220> FEATURE:
<222> LOCATION: 225...233
<223> OTHER INFORMATION: TADG-12 peptide

<400> SEQUENCE: 37

Leu Leu Ser Gln Trp Pro Trp Gln Ala
                5

<210> SEQ ID NO 38
<211> LENGTH: 9
<212> TYPE: PRT
<213> ORGANISM: Homo sapiens
<220> FEATURE:
<222> LOCATION: 252...260
<223> OTHER INFORMATION: TADG-12 peptide

<400> SEQUENCE: 38

Trp Ile Ile Thr Ala Ala His Cys Val
                5

<210> SEQ ID NO 39
<211> LENGTH: 9
<212> TYPE: PRT
<213> ORGANISM: Homo sapiens
<220> FEATURE:
<222> LOCATION: 356...364
<223> OTHER INFORMATION: TADG-12 peptide

<400> SEQUENCE: 39

Val Leu Asn His Ala Ala Val Pro Leu
                5

<210> SEQ ID NO 40
<211> LENGTH: 9
<212> TYPE: PRT
<213> ORGANISM: Homo sapiens
<220> FEATURE:
<222> LOCATION: 176...184
<223> OTHER INFORMATION: TADG-12 peptide

<400> SEQUENCE: 40

Leu Leu Pro Asp Asp Lys Val Thr Ala
                5

<210> SEQ ID NO 41
<211> LENGTH: 9
<212> TYPE: PRT
<213> ORGANISM: Homo sapiens
<220> FEATURE:
<222> LOCATION: 13...21
<223> OTHER INFORMATION: TADG-12 peptide

<400> SEQUENCE: 41

Phe Ser Phe Arg Ser Leu Phe Gly Leu
                5
```

```
<210> SEQ ID NO 42
<211> LENGTH: 9
<212> TYPE: PRT
<213> ORGANISM: Homo sapiens
<220> FEATURE:
<222> LOCATION: 151...159
<223> OTHER INFORMATION: TADG-12 peptide

<400> SEQUENCE: 42

Tyr Val Ser Ser Asp Asn Leu Arg Val
                5

<210> SEQ ID NO 43
<211> LENGTH: 9
<212> TYPE: PRT
<213> ORGANISM: Homo sapiens
<220> FEATURE:
<222> LOCATION: 436...444
<223> OTHER INFORMATION: TADG-12 peptide

<400> SEQUENCE: 43

Arg Val Thr Ser Phe Leu Asp Trp Ile
                5

<210> SEQ ID NO 44
<211> LENGTH: 9
<212> TYPE: PRT
<213> ORGANISM: Homo sapiens
<220> FEATURE:
<222> LOCATION: 234...242
<223> OTHER INFORMATION: TADG-12 peptide

<400> SEQUENCE: 44

Ser Leu Gln Phe Gln Gly Tyr His Leu
                5

<210> SEQ ID NO 45
<211> LENGTH: 9
<212> TYPE: PRT
<213> ORGANISM: Homo sapiens
<220> FEATURE:
<222> LOCATION: 181...189
<223> OTHER INFORMATION: TADG-12 peptide

<400> SEQUENCE: 45

Lys Val Thr Ala Leu His His Ser Val
                5

<210> SEQ ID NO 46
<211> LENGTH: 9
<212> TYPE: PRT
<213> ORGANISM: Homo sapiens
<220> FEATURE:
<222> LOCATION: 183...191
<223> OTHER INFORMATION: TADG-12 peptide

<400> SEQUENCE: 46

Thr Ala Leu His His Ser Val Tyr Val
                5

<210> SEQ ID NO 47
<211> LENGTH: 9
<212> TYPE: PRT
<213> ORGANISM: Homo sapiens
<220> FEATURE:
<222> LOCATION: 411...419
<223> OTHER INFORMATION: TADG-12 peptide

<400> SEQUENCE: 47
```

```
Arg Leu Trp Lys Leu Val Gly Ala Thr
                5
```

<210> SEQ ID NO 48
<211> LENGTH: 9
<212> TYPE: PRT
<213> ORGANISM: Homo sapiens
<220> FEATURE:
<222> LOCATION: 60...68
<223> OTHER INFORMATION: TADG-12 peptide

<400> SEQUENCE: 48

```
Leu Ile Leu Ala Leu Ala Ile Gly Leu
                5
```

<210> SEQ ID NO 49
<211> LENGTH: 9
<212> TYPE: PRT
<213> ORGANISM: Homo sapiens
<220> FEATURE:
<222> LOCATION: 227...235
<223> OTHER INFORMATION: TADG-12 peptide

<400> SEQUENCE: 49

```
Ser Gln Trp Pro Trp Gln Ala Ser Leu
                5
```

<210> SEQ ID NO 50
<211> LENGTH: 9
<212> TYPE: PRT
<213> ORGANISM: Homo sapiens
<220> FEATURE:
<222> LOCATION: 301...309
<223> OTHER INFORMATION: TADG-12 peptide

<400> SEQUENCE: 50

```
Arg Leu Gly Asn Asp Ile Ala Leu Met
                5
```

<210> SEQ ID NO 51
<211> LENGTH: 9
<212> TYPE: PRT
<213> ORGANISM: Homo sapiens
<220> FEATURE:
<222> LOCATION: 307...315
<223> OTHER INFORMATION: TADG-12 peptide

<400> SEQUENCE: 51

```
Ala Leu Met Lys Leu Ala Gly Pro Leu
                5
```

<210> SEQ ID NO 52
<211> LENGTH: 9
<212> TYPE: PRT
<213> ORGANISM: Homo sapiens
<220> FEATURE:
<222> LOCATION: 262...270
<223> OTHER INFORMATION: TADG-12 peptide

<400> SEQUENCE: 52

```
Asp Leu Tyr Leu Pro Lys Ser Trp Thr
                5
```

<210> SEQ ID NO 53
<211> LENGTH: 9
<212> TYPE: PRT
<213> ORGANISM: Homo sapiens

```
<220> FEATURE:
<222> LOCATION: 416...424
<223> OTHER INFORMATION: TADG-12 peptide

<400> SEQUENCE: 53

Leu Val Gly Ala Thr Ser Phe Gly Ile
                5

<210> SEQ ID NO 54
<211> LENGTH: 9
<212> TYPE: PRT
<213> ORGANISM: Homo sapiens
<220> FEATURE:
<222> LOCATION: 54...62
<223> OTHER INFORMATION: TADG-12 peptide

<400> SEQUENCE: 54

Ser Leu Gly Ile Ile Ala Leu Ile Leu
                5

<210> SEQ ID NO 55
<211> LENGTH: 9
<212> TYPE: PRT
<213> ORGANISM: Homo sapiens
<220> FEATURE:
<222> LOCATION: 218...226
<223> OTHER INFORMATION: TADG-12 peptide

<400> SEQUENCE: 55

Ile Val Gly Gly Asn Met Ser Leu Leu
                5

<210> SEQ ID NO 56
<211> LENGTH: 9
<212> TYPE: PRT
<213> ORGANISM: Homo sapiens
<220> FEATURE:
<222> LOCATION: 35...43
<223> OTHER INFORMATION: TADG-12 peptide

<400> SEQUENCE: 56

Ala Val Ala Ala Gln Ile Leu Ser Leu
                5

<210> SEQ ID NO 57
<211> LENGTH: 9
<212> TYPE: PRT
<213> ORGANISM: Homo sapiens
<220> FEATURE:
<222> LOCATION: 271...279
<223> OTHER INFORMATION: TADG-12 peptide

<400> SEQUENCE: 57

Ile Gln Val Gly Leu Val Ser Leu Leu
                5

<210> SEQ ID NO 58
<211> LENGTH: 9
<212> TYPE: PRT
<213> ORGANISM: Homo sapiens
<220> FEATURE:
<222> LOCATION: 397...405
<223> OTHER INFORMATION: TADG-12 peptide

<400> SEQUENCE: 58

Cys Gln Gly Asp Ser Gly Gly Pro Leu
                5
```

```
<210> SEQ ID NO 59
<211> LENGTH: 9
<212> TYPE: PRT
<213> ORGANISM: Homo sapiens
<220> FEATURE:
<222> LOCATION: 270...278
<223> OTHER INFORMATION: TADG-12 peptide

<400> SEQUENCE: 59

Thr Ile Gln Val Gly Leu Val Ser Leu
                5

<210> SEQ ID NO 60
<211> LENGTH: 9
<212> TYPE: PRT
<213> ORGANISM: Homo sapiens
<220> FEATURE:
<222> LOCATION: 56...64
<223> OTHER INFORMATION: TADG-12 peptide

<400> SEQUENCE: 60

Gly Ile Ile Ala Leu Ile Leu Ala Leu
                5

<210> SEQ ID NO 61
<211> LENGTH: 9
<212> TYPE: PRT
<213> ORGANISM: Homo sapiens
<220> FEATURE:
<222> LOCATION: 110...118
<223> OTHER INFORMATION: TADG-12 peptide

<400> SEQUENCE: 61

Arg Val Gly Gly Gln Asn Ala Val Leu
                5

<210> SEQ ID NO 62
<211> LENGTH: 9
<212> TYPE: PRT
<213> ORGANISM: Homo sapiens
<220> FEATURE:
<222> LOCATION: 217...225
<223> OTHER INFORMATION: TADG-12 peptide

<400> SEQUENCE: 62

Arg Ile Val Gly Gly Asn Met Ser Leu
                5

<210> SEQ ID NO 63
<211> LENGTH: 9
<212> TYPE: PRT
<213> ORGANISM: Homo sapiens
<220> FEATURE:
<222> LOCATION: 130...138
<223> OTHER INFORMATION: TADG-12 peptide

<400> SEQUENCE: 63

Cys Ser Asp Asp Trp Lys Gly His Tyr
                5

<210> SEQ ID NO 64
<211> LENGTH: 9
<212> TYPE: PRT
<213> ORGANISM: Homo sapiens
<220> FEATURE:
<222> LOCATION: 8...16
<223> OTHER INFORMATION: TADG-12 peptide
```

```
<400> SEQUENCE: 64

Ala Val Glu Ala Pro Phe Ser Phe Arg
                5

<210> SEQ ID NO 65
<211> LENGTH: 9
<212> TYPE: PRT
<213> ORGANISM: Homo sapiens
<220> FEATURE:
<222> LOCATION: 328...336
<223> OTHER INFORMATION: TADG-12 peptide

<400> SEQUENCE: 65

Asn Ser Glu Glu Asn Phe Pro Asp Gly
                5

<210> SEQ ID NO 66
<211> LENGTH: 9
<212> TYPE: PRT
<213> ORGANISM: Homo sapiens
<220> FEATURE:
<222> LOCATION: 3...11
<223> OTHER INFORMATION: TADG-12 peptide

<400> SEQUENCE: 66

Glu Asn Asp Pro Pro Ala Val Glu Ala
                5

<210> SEQ ID NO 67
<211> LENGTH: 9
<212> TYPE: PRT
<213> ORGANISM: Homo sapiens
<220> FEATURE:
<222> LOCATION: 98...106
<223> OTHER INFORMATION: TADG-12 peptide

<400> SEQUENCE: 67

Asp Cys Lys Asp Gly Glu Asp Glu Tyr
                5

<210> SEQ ID NO 68
<211> LENGTH: 9
<212> TYPE: PRT
<213> ORGANISM: Homo sapiens
<220> FEATURE:
<222> LOCATION: 346...354
<223> OTHER INFORMATION: TADG-12 peptide

<400> SEQUENCE: 68

Ala Thr Glu Asp Gly Gly Asp Ala Ser
                5

<210> SEQ ID NO 69
<211> LENGTH: 9
<212> TYPE: PRT
<213> ORGANISM: Homo sapiens
<220> FEATURE:
<222> LOCATION: 360...368
<223> OTHER INFORMATION: TADG-12 peptide

<400> SEQUENCE: 69

Ala Ala Val Pro Leu Ile Ser Asn Lys
                5

<210> SEQ ID NO 70
<211> LENGTH: 9
<212> TYPE: PRT
```

```
<213> ORGANISM: Homo sapiens
<220> FEATURE:
<222> LOCATION: 153...161
<223> OTHER INFORMATION: TADG-12 peptide

<400> SEQUENCE: 70

Ser Ser Asp Asn Leu Arg Val Ser Ser
                5

<210> SEQ ID NO 71
<211> LENGTH: 9
<212> TYPE: PRT
<213> ORGANISM: Homo sapiens
<220> FEATURE:
<222> LOCATION: 182...190
<223> OTHER INFORMATION: TADG-12 peptide

<400> SEQUENCE: 71

Val Thr Ala Leu His His Ser Val Tyr
                5

<210> SEQ ID NO 72
<211> LENGTH: 9
<212> TYPE: PRT
<213> ORGANISM: Homo sapiens
<220> FEATURE:
<222> LOCATION: 143...151
<223> OTHER INFORMATION: TADG-12 peptide

<400> SEQUENCE: 72

Cys Ala Gln Leu Gly Phe Pro Ser Tyr
                5

<210> SEQ ID NO 73
<211> LENGTH: 9
<212> TYPE: PRT
<213> ORGANISM: Homo sapiens
<220> FEATURE:
<222> LOCATION: 259...267
<223> OTHER INFORMATION: TADG-12 peptide

<400> SEQUENCE: 73

Cys Val Tyr Asp Leu Tyr Leu Pro Lys
                5

<210> SEQ ID NO 74
<211> LENGTH: 9
<212> TYPE: PRT
<213> ORGANISM: Homo sapiens
<220> FEATURE:
<222> LOCATION: 369...377
<223> OTHER INFORMATION: TADG-12 peptide

<400> SEQUENCE: 74

Ile Cys Asn His Arg Asp Val Tyr Gly
                5

<210> SEQ ID NO 75
<211> LENGTH: 9
<212> TYPE: PRT
<213> ORGANISM: Homo sapiens
<220> FEATURE:
<222> LOCATION: 278...286
<223> OTHER INFORMATION: TADG-12 peptide

<400> SEQUENCE: 75

Leu Leu Asp Asn Pro Ala Pro Ser His
                5
```

```
<210> SEQ ID NO 76
<211> LENGTH: 9
<212> TYPE: PRT
<213> ORGANISM: Homo sapiens
<220> FEATURE:
<222> LOCATION: 426...434
<223> OTHER INFORMATION: TADG-12 peptide

<400> SEQUENCE: 76

Cys Ala Glu Val Asn Lys Pro Gly Val
                 5

<210> SEQ ID NO 77
<211> LENGTH: 9
<212> TYPE: PRT
<213> ORGANISM: Homo sapiens
<220> FEATURE:
<222> LOCATION: 32...40
<223> OTHER INFORMATION: TADG-12 peptide

<400> SEQUENCE: 77

Asp Ala Asp Ala Val Ala Ala Gln Ile
                 5

<210> SEQ ID NO 78
<211> LENGTH: 9
<212> TYPE: PRT
<213> ORGANISM: Homo sapiens
<220> FEATURE:
<222> LOCATION: 406...414
<223> OTHER INFORMATION: TADG-12 peptide

<400> SEQUENCE: 78

Val Cys Gln Glu Arg Arg Leu Trp Lys
                 5

<210> SEQ ID NO 79
<211> LENGTH: 9
<212> TYPE: PRT
<213> ORGANISM: Homo sapiens
<220> FEATURE:
<222> LOCATION: 329...337
<223> OTHER INFORMATION: TADG-12 peptide

<400> SEQUENCE: 79

Ser Glu Glu Asn Phe Pro Asp Gly Lys
                 5

<210> SEQ ID NO 80
<211> LENGTH: 9
<212> TYPE: PRT
<213> ORGANISM: Homo sapiens
<220> FEATURE:
<222> LOCATION: 303...311
<223> OTHER INFORMATION: TADG-12 peptide

<400> SEQUENCE: 80

Gly Asn Asp Ile Ala Leu Met Lys Leu
                 5

<210> SEQ ID NO 81
<211> LENGTH: 9
<212> TYPE: PRT
<213> ORGANISM: Homo sapiens
<220> FEATURE:
<222> LOCATION: 127...135
<223> OTHER INFORMATION: TADG-12 peptide
```

```
<400> SEQUENCE: 81

Lys Thr Met Cys Ser Asp Asp Trp Lys
                5

<210> SEQ ID NO 82
<211> LENGTH: 9
<212> TYPE: PRT
<213> ORGANISM: Homo sapiens
<220> FEATURE:
<222> LOCATION: 440...448
<223> OTHER INFORMATION: TADG-12 peptide

<400> SEQUENCE: 82

Phe Leu Asp Trp Ile His Glu Gln Met
                5

<210> SEQ ID NO 83
<211> LENGTH: 9
<212> TYPE: PRT
<213> ORGANISM: Homo sapiens
<220> FEATURE:
<222> LOCATION: 433...441
<223> OTHER INFORMATION: TADG-12 peptide

<400> SEQUENCE: 83

Val Tyr Thr Arg Val Thr Ser Phe Leu
                5

<210> SEQ ID NO 84
<211> LENGTH: 9
<212> TYPE: PRT
<213> ORGANISM: Homo sapiens
<220> FEATURE:
<222> LOCATION: 263...271
<223> OTHER INFORMATION: TADG-12 peptide

<400> SEQUENCE: 84

Leu Tyr Leu Pro Lys Ser Trp Thr Ile
                5

<210> SEQ ID NO 85
<211> LENGTH: 9
<212> TYPE: PRT
<213> ORGANISM: Homo sapiens
<220> FEATURE:
<222> LOCATION: 169...177
<223> OTHER INFORMATION: TADG-12 peptide

<400> SEQUENCE: 85

Glu Phe Val Ser Ile Asp His Leu Leu
                5

<210> SEQ ID NO 86
<211> LENGTH: 9
<212> TYPE: PRT
<213> ORGANISM: Homo sapiens
<220> FEATURE:
<222> LOCATION: 296...304
<223> OTHER INFORMATION: TADG-12 peptide

<400> SEQUENCE: 86

Lys Tyr Lys Pro Lys Arg Leu Gly Asn
                5

<210> SEQ ID NO 87
<211> LENGTH: 9
```

-continued

```
<212> TYPE: PRT
<213> ORGANISM: Homo sapiens
<220> FEATURE:
<222> LOCATION: 16...24
<223> OTHER INFORMATION: TADG-12 peptide

<400> SEQUENCE: 87

Arg Ser Leu Phe Gly Leu Asp Asp Leu
                 5

<210> SEQ ID NO 88
<211> LENGTH: 9
<212> TYPE: PRT
<213> ORGANISM: Homo sapiens
<220> FEATURE:
<222> LOCATION: 267...275
<223> OTHER INFORMATION: TADG-12 peptide

<400> SEQUENCE: 88

Lys Ser Trp Thr Ile Gln Val Gly Leu
                 5

<210> SEQ ID NO 89
<211> LENGTH: 9
<212> TYPE: PRT
<213> ORGANISM: Homo sapiens
<220> FEATURE:
<222> LOCATION: 81...89
<223> OTHER INFORMATION: TADG-12 peptide

<400> SEQUENCE: 89

Arg Ser Ser Phe Lys Cys Ile Glu Leu
                 5

<210> SEQ ID NO 90
<211> LENGTH: 9
<212> TYPE: PRT
<213> ORGANISM: Homo sapiens
<220> FEATURE:
<222> LOCATION: 375...383
<223> OTHER INFORMATION: TADG-12 peptide

<400> SEQUENCE: 90

Val Tyr Gly Gly Ile Ile Ser Pro Ser
                 5

<210> SEQ ID NO 91
<211> LENGTH: 9
<212> TYPE: PRT
<213> ORGANISM: Homo sapiens
<220> FEATURE:
<222> LOCATION: 110...118
<223> OTHER INFORMATION: TADG-12 peptide

<400> SEQUENCE: 91

Arg Val Gly Gly Gln Asn Ala Val Leu
                 5

<210> SEQ ID NO 92
<211> LENGTH: 9
<212> TYPE: PRT
<213> ORGANISM: Homo sapiens
<220> FEATURE:
<222> LOCATION: 189...197
<223> OTHER INFORMATION: TADG-12 peptide

<400> SEQUENCE: 92

Val Tyr Val Arg Glu Gly Cys Ala Ser
```

```
<210> SEQ ID NO 93
<211> LENGTH: 9
<212> TYPE: PRT
<213> ORGANISM: Homo sapiens
<220> FEATURE:
<222> LOCATION: 165...173
<223> OTHER INFORMATION: TADG-12 peptide

<400> SEQUENCE: 93

Gln Phe Arg Glu Glu Phe Val Ser Ile
                5

<210> SEQ ID NO 94
<211> LENGTH: 9
<212> TYPE: PRT
<213> ORGANISM: Homo sapiens
<220> FEATURE:
<222> LOCATION: 10...18
<223> OTHER INFORMATION: TADG-12 peptide

<400> SEQUENCE: 94

Glu Ala Pro Phe Ser Phe Arg Ser Leu
                5

<210> SEQ ID NO 95
<211> LENGTH: 9
<212> TYPE: PRT
<213> ORGANISM: Homo sapiens
<220> FEATURE:
<222> LOCATION: 407...415
<223> OTHER INFORMATION: TADG-12 peptide

<400> SEQUENCE: 95

Cys Gln Glu Arg Arg Leu Trp Lys Leu
                5

<210> SEQ ID NO 96
<211> LENGTH: 9
<212> TYPE: PRT
<213> ORGANISM: Homo sapiens
<220> FEATURE:
<222> LOCATION: 381...389
<223> OTHER INFORMATION: TADG-12 peptide

<400> SEQUENCE: 96

Ser Pro Ser Met Leu Cys Ala Gly Tyr
                5

<210> SEQ ID NO 97
<211> LENGTH: 9
<212> TYPE: PRT
<213> ORGANISM: Homo sapiens
<220> FEATURE:
<222> LOCATION: 375...383
<223> OTHER INFORMATION: TADG-12 peptide

<400> SEQUENCE: 97

Val Tyr Gly Gly Ile Ile Ser Pro Ser
                5

<210> SEQ ID NO 98
<211> LENGTH: 9
<212> TYPE: PRT
<213> ORGANISM: Homo sapiens
<220> FEATURE:
<222> LOCATION: 381...389
```

<223> OTHER INFORMATION: TADG-12 peptide

<400> SEQUENCE: 98

Ser Pro Ser Met Leu Cys Ala Gly Tyr
                5

<210> SEQ ID NO 99
<211> LENGTH: 9
<212> TYPE: PRT
<213> ORGANISM: Homo sapiens
<220> FEATURE:
<222> LOCATION: 362...370
<223> OTHER INFORMATION: TADG-12 peptide

<400> SEQUENCE: 99

Val Pro Leu Ile Ser Asn Lys Ile Cys
                5

<210> SEQ ID NO 100
<211> LENGTH: 9
<212> TYPE: PRT
<213> ORGANISM: Homo sapiens
<220> FEATURE:
<222> LOCATION: 373...381
<223> OTHER INFORMATION: TADG-12 peptide

<400> SEQUENCE: 100

Arg Asp Val Tyr Gly Gly Ile Ile Ser
                5

<210> SEQ ID NO 101
<211> LENGTH: 9
<212> TYPE: PRT
<213> ORGANISM: Homo sapiens
<220> FEATURE:
<222> LOCATION: 283...291
<223> OTHER INFORMATION: TADG-12 peptide

<400> SEQUENCE: 101

Ala Pro Ser His Leu Val Glu Lys Ile
                5

<210> SEQ ID NO 102
<211> LENGTH: 9
<212> TYPE: PRT
<213> ORGANISM: Homo sapiens
<220> FEATURE:
<222> LOCATION: 177...185
<223> OTHER INFORMATION: TADG-12 peptide

<400> SEQUENCE: 102

Leu Pro Asp Asp Lys Val Thr Ala Leu
                5

<210> SEQ ID NO 103
<211> LENGTH: 9
<212> TYPE: PRT
<213> ORGANISM: Homo sapiens
<220> FEATURE:
<222> LOCATION: 47...55
<223> OTHER INFORMATION: TADG-12 peptide

<400> SEQUENCE: 103

Glu Val Phe Ser Gln Ser Ser Ser Leu
                5

<210> SEQ ID NO 104

<211> LENGTH: 9
<212> TYPE: PRT
<213> ORGANISM: Homo sapiens
<220> FEATURE:
<222> LOCATION: 36...44
<223> OTHER INFORMATION: TADG-12 peptide

<400> SEQUENCE: 104

Val Ala Ala Gln Ile Leu Ser Leu Leu
                5

<210> SEQ ID NO 105
<211> LENGTH: 9
<212> TYPE: PRT
<213> ORGANISM: Homo sapiens
<220> FEATURE:
<222> LOCATION: 255...263
<223> OTHER INFORMATION: TADG-12 peptide

<400> SEQUENCE: 105

Thr Ala Ala His Cys Val Tyr Asp Leu
                5

<210> SEQ ID NO 106
<211> LENGTH: 9
<212> TYPE: PRT
<213> ORGANISM: Homo sapiens
<220> FEATURE:
<222> LOCATION: 138...146
<223> OTHER INFORMATION: TADG-12 peptide

<400> SEQUENCE: 106

Tyr Ala Asn Val Ala Cys Ala Gln Leu
                5

<210> SEQ ID NO 107
<211> LENGTH: 9
<212> TYPE: PRT
<213> ORGANISM: Homo sapiens
<220> FEATURE:
<222> LOCATION: 195...203
<223> OTHER INFORMATION: TADG-12 peptide

<400> SEQUENCE: 107

Cys Ala Ser Gly His Val Val Thr Leu
                5

<210> SEQ ID NO 108
<211> LENGTH: 9
<212> TYPE: PRT
<213> ORGANISM: Homo sapiens
<220> FEATURE:
<222> LOCATION: 215...223
<223> OTHER INFORMATION: TADG-12 peptide

<400> SEQUENCE: 108

Ser Ser Arg Ile Val Gly Gly Asn Met
                5

<210> SEQ ID NO 109
<211> LENGTH: 9
<212> TYPE: PRT
<213> ORGANISM: Homo sapiens
<220> FEATURE:
<222> LOCATION: 298...306
<223> OTHER INFORMATION: TADG-12 peptide

<400> SEQUENCE: 109

Lys Pro Lys Arg Leu Gly Asn Asp Ile
                5

<210> SEQ ID NO 110
<211> LENGTH: 9
<212> TYPE: PRT
<213> ORGANISM: Homo sapiens
<220> FEATURE:
<222> LOCATION: 313...321
<223> OTHER INFORMATION: TADG-12 peptide

<400> SEQUENCE: 110

Gly Pro Leu Thr Phe Asn Glu Met Ile
                5

<210> SEQ ID NO 111
<211> LENGTH: 9
<212> TYPE: PRT
<213> ORGANISM: Homo sapiens
<220> FEATURE:
<222> LOCATION: 108...116
<223> OTHER INFORMATION: TADG-12 peptide

<400> SEQUENCE: 111

Cys Val Arg Val Gly Gly Gln Asn Ala
                5

<210> SEQ ID NO 112
<211> LENGTH: 9
<212> TYPE: PRT
<213> ORGANISM: Homo sapiens
<220> FEATURE:
<222> LOCATION: 294...302
<223> OTHER INFORMATION: TADG-12 peptide

<400> SEQUENCE: 112

His Ser Lys Tyr Lys Pro Lys Arg Leu
                5

<210> SEQ ID NO 113
<211> LENGTH: 9
<212> TYPE: PRT
<213> ORGANISM: Homo sapiens
<220> FEATURE:
<222> LOCATION: 265...273
<223> OTHER INFORMATION: TADG-12 peptide

<400> SEQUENCE: 113

Leu Pro Lys Ser Trp Thr Ile Gln Val
                5

<210> SEQ ID NO 114
<211> LENGTH: 9
<212> TYPE: PRT
<213> ORGANISM: Homo sapiens
<220> FEATURE:
<222> LOCATION: 88...96
<223> OTHER INFORMATION: TADG-12 peptide

<400> SEQUENCE: 114

Glu Leu Ile Thr Arg Cys Asp Gly Val
                5

<210> SEQ ID NO 115
<211> LENGTH: 9
<212> TYPE: PRT
<213> ORGANISM: Homo sapiens
<220> FEATURE:

```
<222> LOCATION: 79...87
<223> OTHER INFORMATION: TADG-12 peptide

<400> SEQUENCE: 115

Arg Cys Arg Ser Ser Phe Lys Cys Ile
                5

<210> SEQ ID NO 116
<211> LENGTH: 9
<212> TYPE: PRT
<213> ORGANISM: Homo sapiens
<220> FEATURE:
<222> LOCATION: 255...263
<223> OTHER INFORMATION: TADG-12 peptide

<400> SEQUENCE: 116

Thr Ala Ala His Cys Val Tyr Asp Leu
                5

<210> SEQ ID NO 117
<211> LENGTH: 9
<212> TYPE: PRT
<213> ORGANISM: Homo sapiens
<220> FEATURE:
<222> LOCATION: 207...215
<223> OTHER INFORMATION: TADG-12 peptide

<400> SEQUENCE: 117

Ala Cys Gly His Arg Arg Gly Tyr Ser
                5

<210> SEQ ID NO 118
<211> LENGTH: 9
<212> TYPE: PRT
<213> ORGANISM: Homo sapiens
<220> FEATURE:
<222> LOCATION: 154...162
<223> OTHER INFORMATION: TADG-12 peptide

<400> SEQUENCE: 118

Ser Asp Asn Leu Arg Val Ser Ser Leu
                5

<210> SEQ ID NO 119
<211> LENGTH: 9
<212> TYPE: PRT
<213> ORGANISM: Homo sapiens
<220> FEATURE:
<222> LOCATION: 300...308
<223> OTHER INFORMATION: TADG-12 peptide

<400> SEQUENCE: 119

Lys Arg Leu Gly Asn Asp Ile Ala Leu
                5

<210> SEQ ID NO 120
<211> LENGTH: 9
<212> TYPE: PRT
<213> ORGANISM: Homo sapiens
<220> FEATURE:
<222> LOCATION: 435...443
<223> OTHER INFORMATION: TADG-12 peptide

<400> SEQUENCE: 120

Thr Arg Val Thr Ser Phe Leu Asp Trp
                5
```

```
<210> SEQ ID NO 121
<211> LENGTH: 9
<212> TYPE: PRT
<213> ORGANISM: Homo sapiens
<220> FEATURE:
<222> LOCATION: 376...384
<223> OTHER INFORMATION: TADG-12 peptide

<400> SEQUENCE: 121

Tyr Gly Gly Ile Ile Ser Pro Ser Met
              5

<210> SEQ ID NO 122
<211> LENGTH: 9
<212> TYPE: PRT
<213> ORGANISM: Homo sapiens
<220> FEATURE:
<222> LOCATION: 410...418
<223> OTHER INFORMATION: TADG-12 peptide

<400> SEQUENCE: 122

Arg Arg Leu Trp Lys Leu Val Gly Ala
              5

<210> SEQ ID NO 123
<211> LENGTH: 9
<212> TYPE: PRT
<213> ORGANISM: Homo sapiens
<220> FEATURE:
<222> LOCATION: 210...218
<223> OTHER INFORMATION: TADG-12 peptide

<400> SEQUENCE: 123

His Arg Arg Gly Tyr Ser Ser Arg Ile
              5

<210> SEQ ID NO 124
<211> LENGTH: 9
<212> TYPE: PRT
<213> ORGANISM: Homo sapiens
<220> FEATURE:
<222> LOCATION: 109...117
<223> OTHER INFORMATION: TADG-12 peptide

<400> SEQUENCE: 124

Val Arg Val Gly Gly Gln Asn Ala Val
              5

<210> SEQ ID NO 125
<211> LENGTH: 9
<212> TYPE: PRT
<213> ORGANISM: Homo sapiens
<220> FEATURE:
<222> LOCATION: 191...199
<223> OTHER INFORMATION: TADG-12 peptide

<400> SEQUENCE: 125

Val Arg Glu Gly Cys Ala Ser Gly His
              5

<210> SEQ ID NO 126
<211> LENGTH: 9
<212> TYPE: PRT
<213> ORGANISM: Homo sapiens
<220> FEATURE:
<222> LOCATION: 78...86
<223> OTHER INFORMATION: TADG-12 peptide

<400> SEQUENCE: 126
```

Tyr Arg Cys Arg Ser Ser Phe Lys Cys
            5

<210> SEQ ID NO 127
<211> LENGTH: 9
<212> TYPE: PRT
<213> ORGANISM: Homo sapiens
<220> FEATURE:
<222> LOCATION: 113...121
<223> OTHER INFORMATION: TADG-12 peptide

<400> SEQUENCE: 127

Gly Gln Asn Ala Val Leu Gln Val Phe
            5

<210> SEQ ID NO 128
<211> LENGTH: 9
<212> TYPE: PRT
<213> ORGANISM: Homo sapiens
<220> FEATURE:
<222> LOCATION: 91...99
<223> OTHER INFORMATION: TADG-12 peptide

<400> SEQUENCE: 128

Thr Arg Cys Asp Gly Val Ser Asp Cys
            5

<210> SEQ ID NO 129
<211> LENGTH: 9
<212> TYPE: PRT
<213> ORGANISM: Homo sapiens
<220> FEATURE:
<222> LOCATION: 38...46
<223> OTHER INFORMATION: TADG-12 peptide

<400> SEQUENCE: 129

Ala Gln Ile Leu Ser Leu Leu Pro Phe
            5

<210> SEQ ID NO 130
<211> LENGTH: 9
<212> TYPE: PRT
<213> ORGANISM: Homo sapiens
<220> FEATURE:
<222> LOCATION: 211...219
<223> OTHER INFORMATION: TADG-12 peptide

<400> SEQUENCE: 130

Arg Arg Gly Tyr Ser Ser Arg Ile Val
            5

<210> SEQ ID NO 131
<211> LENGTH: 9
<212> TYPE: PRT
<213> ORGANISM: Homo sapiens
<220> FEATURE:
<222> LOCATION: 216...224
<223> OTHER INFORMATION: TADG-12 peptide

<400> SEQUENCE: 131

Ser Arg Ile Val Gly Gly Asn Met Ser
            5

<210> SEQ ID NO 132
<211> LENGTH: 9
<212> TYPE: PRT
<213> ORGANISM: Homo sapiens

```
<220> FEATURE:
<222> LOCATION: 118...126
<223> OTHER INFORMATION: TADG-12 peptide

<400> SEQUENCE: 132

Leu Gln Val Phe Thr Ala Ala Ser Trp
                5

<210> SEQ ID NO 133
<211> LENGTH: 9
<212> TYPE: PRT
<213> ORGANISM: Homo sapiens
<220> FEATURE:
<222> LOCATION: 370...378
<223> OTHER INFORMATION: TADG-12 peptide

<400> SEQUENCE: 133

Cys Asn His Arg Asp Val Tyr Gly Gly
                5

<210> SEQ ID NO 134
<211> LENGTH: 9
<212> TYPE: PRT
<213> ORGANISM: Homo sapiens
<220> FEATURE:
<222> LOCATION: 393...401
<223> OTHER INFORMATION: TADG-12 peptide

<400> SEQUENCE: 134

Gly Val Asp Ser Cys Gln Gly Asp Ser
                5

<210> SEQ ID NO 135
<211> LENGTH: 9
<212> TYPE: PRT
<213> ORGANISM: Homo sapiens
<220> FEATURE:
<222> LOCATION: 235...243
<223> OTHER INFORMATION: TADG-12 peptide

<400> SEQUENCE: 135

Leu Gln Phe Gln Gly Tyr His Leu Cys
                5

<210> SEQ ID NO 136
<211> LENGTH: 9
<212> TYPE: PRT
<213> ORGANISM: Homo sapiens
<220> FEATURE:
<222> LOCATION: 427...435
<223> OTHER INFORMATION: TADG-12 peptide

<400> SEQUENCE: 136

Ala Glu Val Asn Lys Pro Gly Val Tyr
                5

<210> SEQ ID NO 137
<211> LENGTH: 9
<212> TYPE: PRT
<213> ORGANISM: Homo sapiens
<220> FEATURE:
<222> LOCATION: 162...170
<223> OTHER INFORMATION: TADG-12 peptide

<400> SEQUENCE: 137

Leu Glu Gly Gln Phe Arg Glu Glu Phe
                5
```

```
<210> SEQ ID NO 138
<211> LENGTH: 9
<212> TYPE: PRT
<213> ORGANISM: Homo sapiens
<220> FEATURE:
<222> LOCATION: 9...17
<223> OTHER INFORMATION: TADG-12 peptide

<400> SEQUENCE: 138

Val Glu Ala Pro Phe Ser Phe Arg Ser
                5

<210> SEQ ID NO 139
<211> LENGTH: 9
<212> TYPE: PRT
<213> ORGANISM: Homo sapiens
<220> FEATURE:
<222> LOCATION: 318...326
<223> OTHER INFORMATION: TADG-12 peptide

<400> SEQUENCE: 139

Asn Glu Met Ile Gln Pro Val Cys Leu
                5

<210> SEQ ID NO 140
<211> LENGTH: 9
<212> TYPE: PRT
<213> ORGANISM: Homo sapiens
<220> FEATURE:
<222> LOCATION: 256...264
<223> OTHER INFORMATION: TADG-12 peptide

<400> SEQUENCE: 140

Ala Ala His Cys Val Tyr Asp Leu Tyr
                5

<210> SEQ ID NO 141
<211> LENGTH: 9
<212> TYPE: PRT
<213> ORGANISM: Homo sapiens
<220> FEATURE:
<222> LOCATION: 46...54
<223> OTHER INFORMATION: TADG-12 peptide

<400> SEQUENCE: 141

Phe Glu Val Phe Ser Gln Ser Ser Ser
                5

<210> SEQ ID NO 142
<211> LENGTH: 9
<212> TYPE: PRT
<213> ORGANISM: Homo sapiens
<220> FEATURE:
<222> LOCATION: 64...72
<223> OTHER INFORMATION: TADG-12 peptide

<400> SEQUENCE: 142

Leu Ala Ile Gly Leu Gly Ile His Phe
                5

<210> SEQ ID NO 143
<211> LENGTH: 9
<212> TYPE: PRT
<213> ORGANISM: Homo sapiens
<220> FEATURE:
<222> LOCATION: 192...200
<223> OTHER INFORMATION: TADG-12 peptide
```

```
<400> SEQUENCE: 143

Arg Glu Gly Cys Ala Ser Gly His Val
                5

<210> SEQ ID NO 144
<211> LENGTH: 9
<212> TYPE: PRT
<213> ORGANISM: Homo sapiens
<220> FEATURE:
<222> LOCATION: 330...338
<223> OTHER INFORMATION: TADG-12 peptide

<400> SEQUENCE: 144

Glu Glu Asn Phe Pro Asp Gly Lys Val
                5

<210> SEQ ID NO 145
<211> LENGTH: 9
<212> TYPE: PRT
<213> ORGANISM: Homo sapiens
<220> FEATURE:
<222> LOCATION: 182...190
<223> OTHER INFORMATION: TADG-12 peptide

<400> SEQUENCE: 145

Val Thr Ala Leu His His Ser Val Tyr
                5

<210> SEQ ID NO 146
<211> LENGTH: 9
<212> TYPE: PRT
<213> ORGANISM: Homo sapiens
<220> FEATURE:
<222> LOCATION: 408...416
<223> OTHER INFORMATION: TADG-12 peptide

<400> SEQUENCE: 146

Gln Glu Arg Arg Leu Trp Lys Leu Val
                5

<210> SEQ ID NO 147
<211> LENGTH: 9
<212> TYPE: PRT
<213> ORGANISM: Homo sapiens
<220> FEATURE:
<222> LOCATION: 206...214
<223> OTHER INFORMATION: TADG-12 peptide

<400> SEQUENCE: 147

Thr Ala Cys Gly His Arg Arg Gly Tyr
                5

<210> SEQ ID NO 148
<211> LENGTH: 9
<212> TYPE: PRT
<213> ORGANISM: Homo sapiens
<220> FEATURE:
<222> LOCATION: 5...13
<223> OTHER INFORMATION: TADG-12 peptide

<400> SEQUENCE: 148

Asp Pro Pro Ala Val Glu Ala Pro Phe
                5

<210> SEQ ID NO 149
<211> LENGTH: 9
<212> TYPE: PRT
```

```
<213> ORGANISM: Homo sapiens
<220> FEATURE:
<222> LOCATION: 261...269
<223> OTHER INFORMATION: TADG-12 peptide

<400> SEQUENCE: 149

Tyr Asp Leu Tyr Leu Pro Lys Ser Trp
                5

<210> SEQ ID NO 150
<211> LENGTH: 9
<212> TYPE: PRT
<213> ORGANISM: Homo sapiens
<220> FEATURE:
<222> LOCATION: 33...41
<223> OTHER INFORMATION: TADG-12 peptide

<400> SEQUENCE: 150

Ala Asp Ala Val Ala Ala Gln Ile Leu
                5

<210> SEQ ID NO 151
<211> LENGTH: 9
<212> TYPE: PRT
<213> ORGANISM: Homo sapiens
<220> FEATURE:
<222> LOCATION: 168...176
<223> OTHER INFORMATION: TADG-12 peptide

<400> SEQUENCE: 151

Glu Glu Phe Val Ser Ile Asp His Leu
                5

<210> SEQ ID NO 152
<211> LENGTH: 9
<212> TYPE: PRT
<213> ORGANISM: Homo sapiens
<220> FEATURE:
<222> LOCATION: 304...312
<223> OTHER INFORMATION: TADG-12 peptide

<400> SEQUENCE: 152

Asn Asp Ile Ala Leu Met Lys Leu Ala
                5

<210> SEQ ID NO 153
<211> LENGTH: 9
<212> TYPE: PRT
<213> ORGANISM: Homo sapiens
<220> FEATURE:
<222> LOCATION: 104...112
<223> OTHER INFORMATION: TADG-12 peptide

<400> SEQUENCE: 153

Asp Glu Tyr Arg Cys Val Arg Val Gly
                5
```

TRANSMEMBRANE SERINE PROTEASE OVEREXPRESSED IN OVARIAN CARCINOMA AND USES THEREOF

CROSS-REFERENCE TO RELATED APPLICATIONS

This is a divisional application of U.S. Ser. No. 09/518,046, filed on Mar. 2, 2000, now U.S. Pat. No. 6,294,663, which is a continuation-in-part patent application and claims the benefit of priority under 35 USC §120 of U.S. Ser. No. 09/261,416. filed Mar. 3, 1999 now U.S. Pat. No. 6,291,663.

BACKGROUND OF THE INVENTION

1. Field of the Invention

The present invention relates generally to the fields of cellular biology and diagnosis of neoplastic disease. More specifically. the present invention relates to a transmembrane serine protease termed Tumor Associated Differentially-Expressed Gene-12 (TADG-12), which is overexpressed in ovarian carcinoma.

2. Description of the Related Art

Tumor cells rely on the expression of a concert of proteases to be released from their primary sites and move to distant sites to inflict lethality. This metastatic nature is the result of an aberrant expression pattern of proteases by tumor cells and also by stromal cells surrounding the tumors [1–3]. For most tumors to become metastatic, they must degrade their surrounding extracellular matrix components, degrade basement membranes to gain access to the bloodstream or lymph system, and repeat this process in reverse fashion to settle in a secondary host site [3–6]. All of these processes rely upon what now appears to be a synchronized protease cascade. In addition, tumor cells use the power of proteases to activate growth and angiogenic factors that allow the tumor to grow progressively [1]. Therefore, much research has been aimed at the identification of tumor-associated proteases and the inhibition of these enzymes for therapeutic means. More importantly, the secreted nature and/or high level expression of many of these proteases allows for their detection at aberrant levels in patient serum, e.g. the prostate-specific antigen (PSA), which allows for early diagnosis of prostate cancer [7].

Proteases have been associated directly with tumor growth, shedding of tumor cells and invasion of target organs. Individual classes of proteases are involved in, but not limited to (1) the digestion of stroma surrounding the initial tumor area, (2) the digestion of the cellular adhesion molecules to allow dissociation of tumor cells; and (3) the invasion of the basement membrane for metastatic growth and the activation of both tumor growth factors and angiogenic factors.

For many forms of cancer, diagnosis and treatment has improved dramatically in the last 10 years. However, the five year survival rate for ovarian cancer remains below 50% due in large part to the vague symptoms which allow for progression of the disease to an advanced stage prior to diagnosis [8]. Although the exploitation of the CA125 antigen has been useful as a marker for monitoring recurrence of ovarian cancer, it has not proven to be an ideal marker for early diagnosis. Therefore, new markers that may be secreted or released from cells and which are highly expressed by ovarian tumors could provide a useful tool for the early diagnosis and for therapeutic intervention in patients with ovarian carcinoma.

The prior art is deficient in the lack of the complete identification of the proteases overexpressed in carcinoma, therefore, deficient in the lack of a tumor marker useful as an indicator of early disease, particularly for ovarian cancers. Specifically, TADG-12, a transmembrane serine protease, has not been previously identified in either nucleic acid or protein form. The present invention fulfills this long-standing need and desire in the art.

SUMMARY OF THE INVENTION

The present invention discloses TADG-12, a new member of the Tumor Associated Differentially-Expressed Gene (TADG) family, and a variant splicing form of TADG-12 (TADG-12V) that could lead to a truncated protein product. TADG-12 is a transmembrane serine protease overexpressed in ovarian carcinoma. The entire cDNA of TADG-12 has been identified (SEQ ID No. 1). This sequence encodes a putative protein of 454 amino acids (SEQ ID No. 2) which includes a potential transmembrane domain, an LDL receptor like domain, a scavenger receptor cysteine rich domain, and a serine protease domain. These features imply that TADG-12 is expressed at the cell surface, and it may be used as a molecular target for therapy or a diagnostic marker.

In one embodiment of the present invention, there is provided a DNA fragment encoding a TADG-12 protein selected from the group consisting of: (a) an isolated DNA fragment which encodes a TADG-12 protein; (b) an isolated DNA fragment which hybridizes to isolated DNA fragment of (a) above and which encodes a TADG-12 protein; and (c) an isolated DNA fragment differing from the isolated DNA fragments of (a) and (b) above in codon sequence due to the degeneracy of the genetic code, and which encodes a TADG-12 protein. Specifically, the DNA fragment has a sequence shown in SEQ ID No. 1 or SEQ ID No. 3.

In another embodiment of the present invention, there is provided a vector/host cell capable of expressing the DNA of the present invention.

In yet another embodiment of the present invention, there is provided an isolated and purified TADG-12 protein encoded by DNA selected from the group consisting of: (a) isolated DNA which encodes a TADG-12 protein; (b) isolated DNA which hybridizes to isolated DNA of (a) above and which encodes a TADG-12 protein; and (c) isolated DNA differing from the isolated DNAs of (a) and (b) above in codon sequence due to the degeneracy of the genetic code, and which encodes a TADG-12 protein. Specifically, the TADG-12 protein has an amino acid sequence shown in SEQ ID No. 2 or SEQ ID No. 4.

In still yet another embodiment of the present invention, there is provided a method for detecting expression of a TADG-12 protein, comprising the steps of: (a) contacting mRNA obtained from the cell with the labeled hybridization probe; and (b) detecting hybridization of the probe with the mRNA.

The present invention further provides methods for diagnosing a cancer or other malignant hyperplasia by detecting the TADG-12 protein or mRNA disclosed herein.

In still another embodiment of the present invention, there is provided a method of inhibiting expression of endogenous TADG-12 mRNA in a cell by introducing a vector into the cell, wherein the vector comprises a DNA fragment of TADG-12 in opposite orientation operably linked to elements necessary for expression.

In still yet another embodiment of the present invention, there is provided a method of inhibiting expression of a TADG-12 protein in a cell by introducing an antibody directed against a TADG-12 protein or fragment thereof.

In still yet another embodiment of the present invention, there is provided a method of targeted therapy by administering a compound having a targeting moiety specific for a TADG-12 protein and a therapeutic moiety. Specifically, the TADG-12 protein has an amino acid sequence shown in SEQ ID No. 2 or SEQ ID No. 4.

The present invention still further provides a method of vaccinating an individual against TADG-12 by inoculating the individual with a TADG-12 protein or fragment thereof. Specifically, the TADG-12 protein has an amino acid sequence shown in SEQ ID No. 2 or SEQ ID No. 4. The TADG-12 fragment includes the truncated form of TADG-12V peptide having a sequence shown in SEQ ID No. 8, and a 9-residue up to 12-residue fragment of TADG-12 protein.

In yet another embodiment of the present invention, there is provided an immunogenic composition, comprising an immunogenic fragment of a TADG-12 protein and an appropriate adjuvant. The TADG-12 fragment includes the truncated form of TADG-12V peptide having a sequence shown in SEQ ID No. 8, and a 9-residue up to 12-residue fragment of TADG-12 protein.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1B shows that TADG-12 was subcloned from the 180 bp band while the larger 300 bp band was designated TADG-12V. The sequences were found to overlap for 180 bp (SEQ ID No. 5 for nucleotide sequence, SEQ ID No. 6 for deduced amino acid sequence) with the 300 bp TADG-12V (SEQ ID No. 7 for nucleotide sequence, SEQ ID No. 8 for deduced amino acid sequence) having an additional insert of 133 bases. This insertion (vertical arrow) leads to a frame shift, which causes the TADG-12V transcript to potentially produce a truncated form of TADG-12 with a variant amino acid sequence.

FIG. 4 shows the entire cDNA sequence for TADG-12 (SEQ ID No. 1) with its predicted open reading frame of 454 amino acids (SEQ ID No. 2). Within the nucleotide sequence, the Kozak's consensus sequence for the initiation of translation and the poly-adenylation signal are underlined. In the protein sequence, a potential transmembrane domain is boxed. The LDLR-A domain is underlined with a solid line. The SRCR domain is underlined with a broken line. The residues of the catalytic triad of the serine protease domain are circled, and the beginning of the catalytic domain is marked with an arrow designated as a potential proteolytic cleavage site. The * represents the stop codon that terminates translation.

FIG. 5A shows the 35 amino acid LDLR-A domain of TADG-12 (SEQ ID No. 13) aligned with other LDLR-A motifs from the serine protease TMPRSS2 (U75329, SEQ ID No. 14), the complement subunit C8 (P07358, SEQ ID No. 9), two LDLR-A domains of the glycoprotein GP300 (P98164, SEQ ID Nos. 11–12), and the serine protease matriptase (AF118224, SEQ ID No. 10). TADG-12 has its highest similarity with the other serine proteases for which it is 54% similar to TMPRSS2 and 53% similar to matriptase. The highly conserved cysteine residues are shown in bold type. FIG. 5B shows the SRCR domain of TADG-12 (SEQ ID No. 17) aligned with other domain family members including the human macrophage scavenger receptor (P21757, SEQ ID No. 16), human enterokinase (P98073, SEQ ID No. 19), bovine enterokinase (P21758, SEQ ID No. 15). and the serine protease TMPRSS2 (SEQ ID No. 18). Again, TADG-12 shows its highest similarity within this region to the protease TMPRSS2 at 43%. FIG. 5C shows the protease domain of TADG-12 (SEQ ID No. 23) in alignment with other human serine proteases including protease M (U62801, SEQ ID No. 20), trypsinogen I (P07477, SEQ ID No. 21), plasma kallikrein (P03952, SEQ ID No. 22), hepsin (P05981, SEQ ID No. 25), and TMPRSS2 (SEQ ID No. 24). Cons represents the consensus sequence for each alignment.

DETAILED DESCRIPTION OF THE INVENTION

Figure 1A:
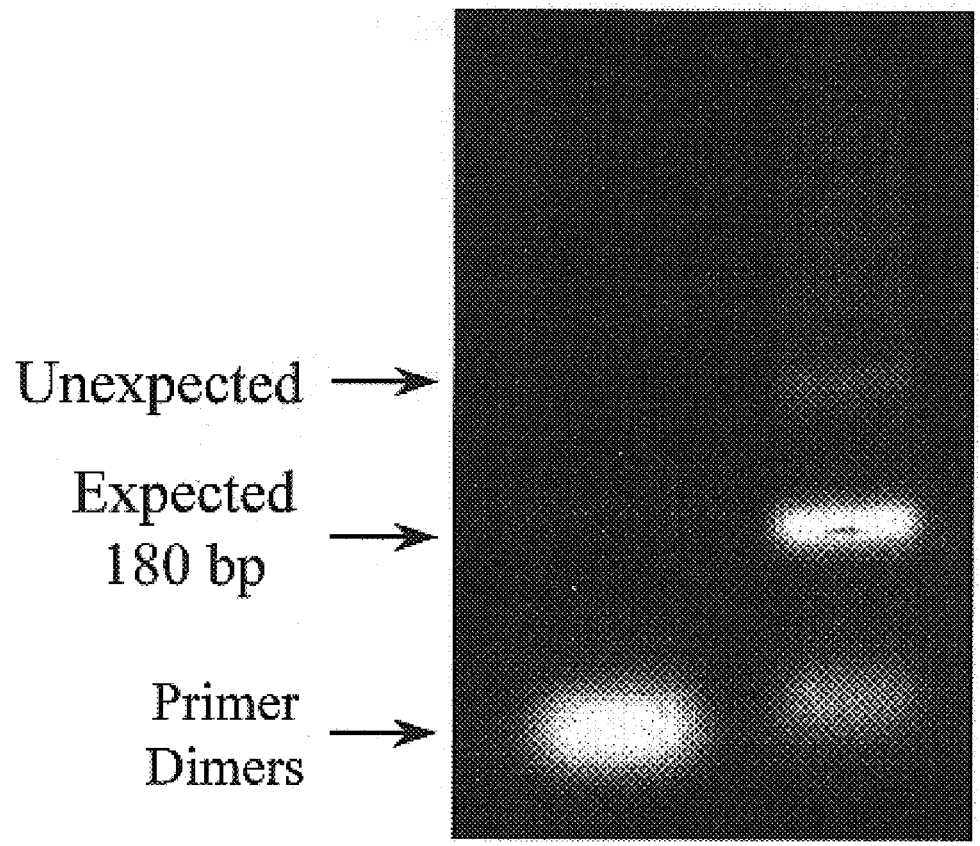
FIG. 1A shows that the expected PCR product of approximately 180 bp and the unexpected PCR product of approximately 300 bp using the redundant serine protease primers were not amplified from normal ovary cDNA (Lane 1) but were found in abundance from ovarian tumor cDNA (Lane 2). The primer sequences for the PCR reactions are indicated by horizontal arrows.

To examine the serine proteases expressed by ovarian cancers, a PCR based differential display technique was employed utilizing redundant PCR primers designed to the most highly conserved amino acids in these proteins [9]. As a result, a novel cell-surface, multi-domain serine protease, named Tumor Associated Differentially-expressed Gene-12 (TADG-12) was identified. TADG-12 appears to be overexpressed in many ovarian tumors. The extracellular nature of TADG-12 may render tumors susceptible to detection via a TADG-12 specific assay. In addition, a splicing variant of TADG-12, named TADG-12V, was detected at elevated levels in 35% of the tumors that were examined. TADG-12V encodes a truncated form of TADG-12 with an altered amino acid sequence that may be a unique tumor specific target for future therapeutic approaches.

The TADG-12 cDNA is 2413 base pairs long (SEQ ID No. 1) encoding a 454 amino acid protein (SEQ ID No. 2). A variant form, TADG-12V (SEQ ID No. 3), encodes a 294 amino acid protein (SEQ ID No. 4). The availability of the TADG-12 and/or TADG-12V gene opens the way for a number studies that can lead to various applications. For example, the TADG-12 and/or TADG-12V gene can be used as a diagnostic or therapeutic target in ovarian carcinoma and other carcinomas including breast, prostate, lung and colon.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal. "A Practical Guide To Molecular Cloning" (1984).

Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

The amino acid described herein are preferred to be in the "L" isomeric form. However, residues in the "D" isomeric form can be substituted for any L-amino acid residue, as long as the desired functional property of immunoglobulin-binding is retained by the polypeptide. $NH_{5142}$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552–59 (1969), abbreviations for amino acid residues are known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

A "replicon" is any genetic element (e.g., plasmid, chromosome virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes.

Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included near the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast. and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g. Maniatis et al., supra; DNA Cloning. Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

Proteins can also be labeled with a radioactive element or with an enzyme. The radioactive label can be detected by any of the currently available counting procedures. The preferred isotope may be selected from $^3H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized calorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

A particular assay system developed and utilized in the art is known as a receptor assay. In a receptor assay, the material to be assayed is appropriately labeled and then certain cellular test colonies are inoculated with a quantity of both the label after which binding studies are conducted to determine the extent to which the labeled material binds to the cell receptors. In this way, differences in affinity between materials can be ascertained.

An assay useful in the art is known as a "cis/trans" assay. Briefly, this assay employs two genetic constructs, one of which is typically a plasmid that continually expresses a particular receptor of interest when transfected into an appropriate cell line, and the second of which is a plasmid that expresses a reporter such as luciferase, under the control of a receptor/ligand complex. Thus, for example, if it is desired to evaluate a compound as a ligand for a particular receptor, one of the plasmids would be a construct that results in expression of the receptor in the chosen cell line, while the second plasmid would possess a promoter linked to the luciferase gene in which the response element to the particular receptor is inserted. If the compound under test is an agonist for the receptor, the ligand will complex with the receptor, and the resulting complex will bind the response element and initiate transcription of the luciferase gene. The resulting chemiluminescence is then measured photometrically, and dose response curves are obtained and compared to those of known ligands. The foregoing protocol is described in detail in U.S. Pat. No. 4,981,784.

As used herein, the term "host" is meant to include not only prokaryotes but also eukaryotes such as yeast, plant and animal cells. A recombinant DNA molecule or gene which encodes a human TADG-12 protein of the present invention can be used to transform a host using any of the techniques commonly known to those of ordinary skill in the art. Especially preferred is the use of a vector containing coding sequences for the gene which encodes a huma TADG-12 protein of the present invention for purposes of prokaryote transformation. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

In general, expression vectors containing promoter sequences which facilitate the efficient transcription of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

The invention includes a substantially pure DNA encoding a TADG-12 protein. a strand of which DNA will hybridize at high stringency to a probe containing a sequence of at least 15 consecutive nucleotides of the sequence shown in SEQ ID No. 1 or SEQ ID No. 3, The protein encoded by the DNA of this invention may share at least 80% sequence identity (preferably 85%,. more preferably 90%, and most preferably 95%) with the amino acids listed in SEQ ID No. 2 or SEQ ID No. 4, More preferably, the DNA includes the coding sequence of the nucleotides of FIG. 4 (SEQ ID No. 1), or a degenerate variant of such a sequence.

The probe to which the DNA of the invention hybridizes preferably consists of a sequence of at least 20 consecutive nucleotides. more preferably 40 nucleotides, even more preferably 50 nucleotides, and most preferably 100 nucleotides or more (up to 100%) of the coding sequence of the nucleotides listed in FIG. 4 (SEQ ID No. 1) or the complement thereof. Such a probe is useful for detecting expression of TADG-12 in a human cell by a method including the steps of (a) contacting mRNA obtained from the cell with the labeled hybridization probe; and (b) detecting hybridization of the probe with the mRNA.

This invention also includes a substantially pure DNA containing a sequence of at least 15 consecutive nucleotides (preferably 20, more preferably 30, even more preferably 50, and most preferably all) of the region from nucleotides 1 to 2413 of the nucleotides listed in SEQ ID No. 1, or of the region from nucleotides 1 to 2544 of the nucleotides listed in SEQ ID No. 3, The present invention also comprises antisense oligonucleotides directed against this novel DNA. Given the teachings of the present invention, a person having ordinary skill in this art would readily be able to develop antisense oligonucleotides directed against this DNA.

By "high stringency" is meant DNA hybridization and wash conditions characterized by high temperature and low salt concentration, e.g., wash conditions of 65° C. at a salt concentration of approximately 0.1×SSC, or the functional equivalent thereof. For example, high stringency conditions may include hybridization at about 42° C. in the presence of about 50% formamide; a first wash at about 65° C. with about 2×SSC containing 1% SDS; followed by a second wash at about 65° C. with about 0.1×SSC.

By "substantially pure DNA" is meant DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by polymerase chain reaction (PCR) or restriction endonuclease digestion) independent of other sequences. It also includes a recombinant DNA which is part of a hybrid gene encoding additional polypeptide sequence. e.g., a fusion protein. Also included is a recombinant DNA which includes a portion of the nucleotides shown in SEQ ID No. 3 which encodes an alternative splice variant of TADG-12 (TADG-12V).

The DNA may have at least about 70% sequence identity to the coding sequence of the nucleotides listed in SEQ ID No. 1 or SEQ ID No. 3, preferably at least 75% (e.g. at least 80%); and most preferably at least 90%. The identity between two sequences is a direct function of the number of matching or identical positions. When a subunit position in both of the two sequences is occupied by the same monomeric subunit, e.g., if a given position is occupied by an adenine in each of two DNA molecules, then they are identical at that position. For example, if 7 positions in a sequence 10 nucleotides in length are identical to the corresponding positions in a second 10-nucleotide sequence, then the two sequences have 70% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

The present invention comprises a vector comprising a DNA sequence which encodes a human TADG-12 protein and the vector is capable of replication in a host which comprises, in operable linkage: a) an origin of replication; b)

a promoter; and c) a DNA sequence coding for said protein. Preferably, the vector of the present invention contains a portion of the DNA sequence shown in SEQ ID No. 1 or SEQ ID No. 3, A "vector" may be defined as a replicable nucleic acid construct, e.g., a plasmid or viral nucleic acid. Vectors may be used to amplify and/or express nucleic acid encoding a TADG-12 protein. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences which control the termination of transcription and translation. Methods which are well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors. Preferred viral vectors of the invention are those derived from retroviruses, adenovirus, adeno-associated virus, SV40 virus, or herpes viruses.

By a "substantially pure protein" is meant a protein which has been separated from at least some of those components which naturally accompany it. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure TADG-12 protein may be obtained, for example, by extraction from a natural source, by expression of a recombinant nucleic acid encoding an TADG-12 polypeptide; or by chemically synthesizing the protein. Purity can be measured by any appropriate method, e.g., column chromatography such as immunoaffinity chromatography using an antibody specific for TADG-12, polyacrylamide gel electrophoresis, or HPLC analysis. A protein is substantially free of naturally associated components when it is separated from at least some of those contaminants which accompany it in its natural state. Thus, a protein which is chemically synthesized or produced in a cellular system different from the cell from which it naturally originates will be, by definition, substantially free from its naturally associated components. Accordingly, substantially pure proteins include eukaryotic proteins synthesized in *E. coli*, other prokaryotes, or any other organism in which they do not naturally occur.

In addition to substantially full-length proteins, the invention also includes fragments (e.g., antigenic fragments) of the TADG-12 protein. As used herein, "fragment," as applied to a polypeptide, will ordinarily be at least 10 residues, more typically at least 20 residues, and preferably at least 30 (e.g., 50) residues in length, but less than the entire, intact sequence. Fragments of the TADG-12 protein can be generated by methods known to those skilled in the art, e.g., by enzymatic digestion of naturally occurring or recombinant TADG-12 protein, by recombinant DNA techniques using an expression vector that encodes a defined fragment of TADG-12, or by chemical synthesis. The ability of a candidate fragment to exhibit a characteristic of TADG-12 (e.g., binding to an antibody specific for TADG-12) can be assessed by methods described herein. Purified TADG-12 or antigenic fragments of TADG-12 can be used to generate new antibodies or to test existing antibodies (e.g., as positive controls in a diagnostic assay) by employing standard protocols known to those skilled in the art. Included in this invention are polyclonal antisera generated by using TADG-12 or a fragment of TADG-12 as the immunogen in, e.g., rabbits. Standard protocols for monoclonal and polyclonal antibody production known to those skilled in this art are employed. The monoclonal antibodies generated by this procedure can be screened for the ability to identity recombinant TADG-12 cDNA clones, and to distinguish them from known cDNA clones.

Further included in this invention are TADG-12 proteins which are encoded at least in part by portions of SEQ ID No. 1 or SEQ ID No. 3 e.g., products of alternative mRNA splicing or alternative protein processing events, or in which a section of TADG-12 sequence has been deleted. The fragment, or the intact TADG-12 polypeptide, may be covalently linked to another polypeptide, e.g. which acts as a label, a ligand or a means to increase antigenicity.

The invention also includes a polyclonal or monoclonal antibody which specifically binds to TADG-12. The invention encompasses not only an intact monoclonal antibody, but also a n immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin.

In one embodiment, the antibody, or a fragment thereof, may be linked to a toxin or to a detectable label, e.g. a radioactive label, non-radioactive isotopic label, fluorescent label, chemiluminescent label, paramagnetic label, enzyme label, or colorimetric label. Examples of suitable toxins include diphtheria toxin, *Pseudomonas* exotoxin A, ricin, and cholera toxin. Examples of suitable enzyme labels include malate hydrogenase, staphylococcal nuclease delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3$H, $^{125}$I, $^{131}$I, $^{32}$P, $^{35}$S, $^{14}$C, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L. (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415. Examples of suitable fluorescent labels include a fluorescein label, an isothiocyalate label, a rhodamine label, a phycoerythrin label, a phycocyanin label, an allophycocyanin label, an opthaldehyde label, a fluorescamine label, etc. Examples of chemiluminescent labels include a luminal label, an isoluminal label, an aromatic acridinium ester label, an imidazole label, an acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy et al., (1976) Clin. Chim. Acta 70, 1–31; and Schurs et al., (1977) Clin. Chim. Acta 81, 1–40. Coupling techniques mentioned in the latter are the glutaraldehyde method, the periodate method, the dimaleimide method, the m-maleimidobenzyl-N-hydroxy-succinimide ester method. All of these methods are incorporated by reference herein.

Also within the invention is a method of detecting TADG-12 protein in a biological sample, which includes the steps of contacting the sample with the labeled antibody, e.g., radioactively tagged antibody specific for TADG-12, and determining whether the antibody binds to a component of the sample.

As described herein, the invention provides a number of diagnostic advantages and uses. For example, the TADG-12 protein disclosed in the present invention is useful in diagnosing cancer in different tissues since this protein is highly overexpressed in tumor cells. Antibodies (or antigen-binding fragments thereof) which bind to an epitope specific for TADG-12, are useful in a method of detecting TADG-12 protein in a biological sample for diagnosis of cancerous or neoplastic transformation. This method includes the steps of obtaining a biological sample (e.g., cells, blood, plasma, tissue, etc.) from a patient suspected of having cancer, contacting the sample with a labeled antibody (e.g., radioactively tagged antibody) specific for TADG-12, and detecting the TADG-12 protein using standard immunoassay techniques such as an ELISA. Antibody binding to the biological sample indicates that the sample contains a component which specifically binds to an epitope within TADG-12.

Likewise, a standard Northern blot assay can be used to ascertain the relative amounts of TADG-12 mRNA in a cell or tissue obtained from a patient suspected of having cancer, in accordance with conventional Northern hybridization techniques known to those of ordinary skill in the art. This Northern assay uses a hybridization probe, e.g., radiolabelled TADG-12 cDNA, either containing the full-length, single stranded DNA having a sequence complementary to SEQ ID No. 1 or SEQ ID No. 3, or a fragment of that DNA sequence at least 20 (preferably at least 30, more preferably at least 50, and most preferably at least 100 consecutive nucleotides in length). The DNA hybridization probe can be labeled by any of the many different methods known to those skilled in this art.

Antibodies to the TADG-12 protein can be used in an immunoassay to detect increased levels of TADG-12 protein expression in tissues suspected of neoplastic transformation. These same uses can be achieved with Northern blot assays and analyses.

The present invention is directed to DNA fragment encoding a TADG-12 protein selected from the group consisting of: (a) an isolated DNA fragment which encodes a TADG-12 protein; (b) an isolated DNA fragment which hybridizes to isolated DNA fragment of (a) above and which encodes a TADG-12 protein; and (c) an isolated DNA fragment differing from the isolated DNA fragments of (a) and (b) above in codon sequence due to the degeneracy of the genetic code, and which encodes a TADG-12 protein. Preferably, the DNA has the sequence shown in SEQ ID No. 1 or SEQ ID No. 3. More preferably, the DNA encodes a TADG-12 protein having the amino acid sequence shown in SEQ ID No. 2 or SEQ ID No. 4.

The present invention is also directed to a vector and/or a host cell capable of expressing the DNA of the present invention. Preferably, the vector contains DNA encoding a TADG-12 protein having the amino acid sequence shown in SEQ ID No. 2 or SEQ ID No. 4. Representative host cells include bacterial cells, yeast cells, mammalian cells and insect cells.

The present invention is also directed to an isolated and purified TADG-12 protein coded for by DNA selected from the group consisting of: (a) isolated DNA which encodes a TADG-12 protein; (b) isolated DNA which hybridizes to isolated DNA of (a) above and which encodes a TADG-12 protein; and (c) isolated DNA differing from the isolated DNAs of (a) and (b) above in codon sequence due to the degeneracy of the genetic code, and which encodes a TADG-12 protein. Preferably, the isolated and purified TADG-12 protein has the amino acid sequence shown in SEQ ID No. 2 or SEQ ID No. 4.

The present invention is also directed to a method of detecting expression of the TADG-12 protein described herein, comprising the steps of: (a) contacting mRNA obtained from the cell with the labeled hybridization probe; and (b) detecting hybridization of the probe with the mRNA.

A number of potential applications are possible for the TADG-12 gene and gene product including the truncated product TADG-12V.

In one embodiment of the present invention, there is provided a method for diagnosing a cancer by detecting a TADG-12 protein in a biological sample, wherein the presence or absence of a TADG-12 protein indicates the presence or absence of a cancer. Preferably, the biological sample is selected from the group consisting of blood, urine, saliva, tears, interstitial fluid, ascites fluid, tumor tissue biopsy and circulating tumor cells. Still preferably, the detection of TADG-12 protein is by means selected from the group consisting of Northern blot, Western blot, PCR, dot blot, ELIZA sandwich assay, radioimmunoassay, DNA array chips and flow cytometry. Such method is used for detecting an ovarian cancer, breast cancer, lung cancer, colon cancer, prostate cancer and other cancers in which TADG-12 is overexpressed.

In another embodiment of the present invention, there is provided a method for detecting malignant hyperplasia by detecting a TADG-12 protein or TADG-12 mRNA in a biological sample. Further by comprising the TADG-12 protein or TADG-12 mRNA to reference information, a diagnosis or a treatment can be provided. Preferably, PCR amplification is used for detecting TADG-12 mRNA, wherein the primers utilized are selected from the group consisting of SEQ ID Nos. 28–31. Still preferably, detection of a TADG-12 protein is by immunoaffinity to an antibody directed against a TADG-12 protein.

In still another embodiment of the present invention, there is provided a method of inhibiting expression of endogenous TADG-12 mRNA in a cell by introducing a vector comprising a DNA fragment of TADG-12 in opposite orientation operably linked to elements necessary for expression. As a result, the vector produces TADG-12 antisense mRNA in the cell, which hybridizes to endogenous TADG-12 mRNA, thereby inhibiting expression of endogenous TADG-12 mRNA.

In still yet another embodiment of the present invention, there is provided a method of inhibiting expression of a TADG-12 protein by introducing an antibody directed against a TADG-12 protein or fragment thereof. As a result, the binding of the antibody to the TADG-12 protein or fragment thereof inhibits the expression of the TADG-12 protein.

TADG-12 gene products including the truncated form can be used for targeted therapy. Specifically, a compound having a targeting moiety specific for a TADG-12 protein and a therapeutic moiety is administered to an individual in need of such treatment. Preferably, the targeting moiety is selected from the group consisting of an antibody directed against a TADG-12 protein and a ligand or ligand binding domain that binds a TADG-12 protein. The TADG-12 protein has an amino acid sequence shown in SEQ ID No. 2 or SEQ ID No. 4. Still preferably, the therapeutic moiety is selected from the group consisting of a radioisotope, a toxin, a chemotherapeutic agent, an immune stimulant and a cytotoxic agent. Such method can be used for treating an individual having a disease selected from the group consisting of ovarian cancer, lung cancer, prostate cancer, colon cancer and other cancers in which TADG-12 is overexpressed.

In yet another embodiment of the present invention, there is provided a method of vaccinating, or producing an immune response in, an individual against TADG-12 by inoculating the individual with a TADG-12 protein or fragment thereof. Specifically, the TADG-12 protein or fragment thereof lacks TADG-12 activity, and the inoculation elicits an immune response in the individual, thereby vaccinating the individual against TADG-12. Preferably, the individual has a cancer, is suspected of having a cancer or is at risk of getting a cancer. Still preferably, TADG-12 protein has an amino acid sequence shown in SEQ ID No. 2 or SEQ ID No. 4, while TADG-12 fragment has a sequence shown in SEQ ID No. 8, or is a 9-residue fragment up to a 20-residue fragment. Examples of 9-residue fragment are shown in SEQ ID Nos. 35, 36, 55, 56, 83, 84, 97, 98, 119, 120, 122, 123 and 136.

In still yet another embodiment of the present invention, there is provided an immunogenic composition, comprising an immunogenic fragment of a TADG-12 protein and an appropriate adjuvant. Preferably, the immunogenic fragment of the TADG-12 protein has a sequence shown in SEQ ID No. 8, or is a 9-residue fragment up to a 20-residue fragment. Examples of 9-residue fragment are shown in SEQ ID Nos. 35, 36, 55, 56, 83, 84, 97, 98, 119, 120, 122, 123 and 136.

The following examples are given for the purpose of illustrating various embodiments of the invention and are not meant to limit the present invention in any fashion.

EXAMPLE 1
Tissue Collection and Storage

Upon patient hysterectomy, bilateral salpingo-oophorectomy, or surgical removal of neoplastic tissue, the specimen is retrieved and placed on ice. The specimen was then taken to the resident pathologist for isolation and identification of specific tissue samples. Finally, the sample was frozen in liquid nitrogen, logged into the laboratory record and stored at −80° C. Additional specimens were frequently obtained from the Cooperative Human Tissue Network (CHTN). These samples were prepared by the CHTN and shipped on dry ice. Upon arrival, these specimens were logged into the laboratory record and stored at −80° C.

EXAMPLE 2
mRNA Extraction and cDNA Synthesis

Sixty-nine ovarian tumors (4 benign tumors, 10 low malignant potential tumors and 55 carcinomas) and 10 normal ovaries were obtained from surgical specimens and frozen in liquid nitrogen. The human ovarian carcinoma cell lines SW 626 and Caov 3, the human breast carcinoma cell lines MDA-MB-231 and MDA-MB-435S were purchased from the American Type Culture Collection (Rockville, Md.). Cells were cultured to sub-confluency in Dulbecco's modified Eagle's medium, supplemented with 10% (v/v) fetal bovine serum and antibiotics.

Extraction of mRNA and cDNA synthesis were carried out by the methods described previously [14–16]. mRNA was isolated by using a RiboSep mRNA isolation kit (Becton Dickinson Labware). In this procedure, poly A+ mRNA was isolated directly from the tissue lysate using the affinity chromatography media oligo(dT) cellulose. cDNA was synthesized with 5.0 µg of mRNA by random hexamer priming using 1st strand cDNA synthesis kit (CLONTECH).

EXAMPLE 3
PCR with Redundant Primers and Cloning of TADG-12 cDNA

Redundant primers, forward 5'-TGGGTIGTIACIGCIGCICA (CT)TG -3' (SEQ ID No. 26) and reverse 5'-A(AG)IA(AG)IGCIATITCI TTICC-3' (SEQ ID No. 27), for the consensus sequences of amino acids surrounding the catalytic triad for serine proteases were used to compare the PCR products from normal and carcinoma cDNAs. The appropriate bands were ligated into Promega T-vector plasmid and the ligation product was used to transform JM109 cells (Promega) grown on selection media. After selection of individual colonies, they were cultured and plasmid DNA was isolated by means of the Wizard miniprep DNA purification system (Promega). Nucleotide sequencing was performed using PRISM Ready Reaction Dye Deoxy terminator cycle sequence kit (Applied Biosystems). Applied Biosystems Model 373A DNA sequencing system was used for direct cDNA sequence determination.

The original TADG-12 subclone was randomly labeled and used as a probe to screen an ovarian tumor cDNA library by standard hybridization techniques [11,15]. The library was constructed in λZAP using mRNA isolated from the tumor cells of a stage III/grade III ovarian adenocarcinoma patient. Three overlapping clones were obtained which spanned 2315 nucleotides. The final 99 nucleotides encoding the most 3' sequence including the poly A tail was identified by homology with clones available in the GenBank EST database.

EXAMPLE 4
Quantitative PCR

The mRNA overexpression of TADG-12 was determined using a quantitative PCR. Quantitative PCR was performed according to the procedure as previously reported [16]. Oligonucleotide primers were used for: TADG-12, forward 5'-GAAACATGTCCTTGCTC TCG-3' (SEQ ID No. 28) and reverse 5'-ACTAACTTCCACAGCCTCCT-3' (SEQ ID No. 29); the variant TADG-12, forward 5'-TCCAGGTGGGTCTAGTTTCC-3' (SEQ ID No. 30), reverse 5'-CTCTTTGG CTTGTACTTGCT-3' (SEQ ID No. 31); β-tubulin, forward 5'-CGCATCAACGTGTACTACAA -3' (SEQ ID No. 32) and reverse 5'-TACGAGCTGGTGGACTGAGA -3' (SEQ ID No. 33). β-tubulin was utilized as an internal control. The PCR reaction mixture consists of cDNA derived from 50 ng of mRNA, 5 pmol of sense and antisense primers for both the TADG-12 gene and the β-tubulin gene, 200 µmol of dNTPs. 5 µCi of α-$^{32}$PdCTP and 0.25 unit of Taq DNA polymerase with reaction buffer (Promega) in a final volume of 25 µl. The target sequences were amplified in parallel with the β-tubulin gene. Thirty cycles of PCR were carried out in a Thermal Cycler (Perkin-Elmer Cetus). Each cycle of PCR included 30 seconds of denaturation at 94% C. 30 seconds of annealing at 60% C and 30 seconds of extension at 72% C. The PCR products were separated on 2% agarose gels and the radioactivity of each PCR product was determined by using a Phospho Imager (Molecular Dynamics). The present study used the expression ratio (TADG-12/β-tubulin) as measured by phosphoimager to evaluate gene expression and defined the value at mean +2SD of normal ovary as the cut-off value to determine overexpression. The student's t test was used for comparison of the mean values of normal ovary and tumors.

EXAMPLE 5
Sequencing of TADG-12/TADG-12V

Utilizing a plasmid specific primer near the cloning site, sequencing reactions were carried out using PRISM™ Ready Reaction Dye Deoxy™ terminators (Applied Biosystems cat#401384) according to the manufacturer's instructions. Residual dye terminators were removed from the completed sequencing reaction using a Centri-sep™ spin column (Princeton Separation cat.#CS-901). An Applied Biosystems Model 373A DNA Sequencing System was available and was used for sequence analysis.

EXAMPLE 6
Antibody Production

Polyclonal rabbit antibodies were generated by immunization of white New Zealand rabbits with a poly-lysine linked multiple antigen peptide derived from the TADG-12 carboxy-terminal protein sequence $NH_2$-WIHEQMERDLKT-COOH (WIHEQMERDLKT, SEQ ID No. 34). This peptide is present in full length TADG-12, but not TADG-12V. Rabbits were immunized with approximately 100 μg of peptide emulsified in Ribi adjuvant. Subsequent boost immunizations were carried out at 3 and 6 weeks, and rabbit serum was isolated 10 days after the boost inoculations. Sera were tested by dot blot analysis to determine affinity for the TADG-12 specific peptide. Rabbit pre-immune serum was used as a negative control.

EXAMPLE 7
Northern Blot Analysis

10 μg of mRNA were loaded onto a 1% formaldehyde-agarose gel, electrophoresed and blotted on a Hybond-N+ nylon membrane (Amersham). $^{32}$P-labeled cDNA probes were made by Prime-a-Gene Labeling System (Promega). The PCR products amplified by the same primers as above were used for probes. The blots were prehybridized for 30 min and hybridized for 60 min at 68% C with $^{32}$P-labeled cDNA probe in ExpressHyb Hybridization Solution (CLONTECH). Control hybridization to determine relative gel loading was performed with the β-tubulin probe.

Normal human tissues; spleen, thymus, prostate, testis, ovary, small intestine, colon and peripheral blood leukocyte, and normal human fetal tissues; brain, lung, liver and kidney (Human Multiple Tissue Northern Blot; CLONTECH) were also examined by same hybridization procedure.

EXAMPLE 8
Immunohistochemistry

Immunohistochemical staining was performed using a Vectastain Elite ABC Kit (Vector). Formalin fixed and paraffin embedded specimens were routinely deparaffinized and processed using microwave heat treatment in 0.01 M sodium citrate buffer (pH 6.0). The specimens were incubated with normal goat serum in a moist chamber for 30 minutes. TADG-12 peptide antibody was allowed to incubate with the specimens in a moisture chamber for 1 hour. Excess antibody was washed away with phosphate buffered saline. After incubation with biotinylated anti-rabbit IgG for 30 minutes, the sections were then incubated with ABC reagent (Vector) for 30 minutes. The final products were visualized using the AEC substrate system. (DAKO) and sections were counterstained with hematoxylin before mounting. Negative controls were performed by using normal serum instead of the primary antibody.

EXAMPLE 9
Isolation of Catalytic Domain Subclones of TADG-12 and TADG-12 Variant To identify serine proteases that are expressed in ovarian tumors, redundant PCR primers designed to the conserved regions of the catalytic triad of these enzymes were employed. A sense primer designed to the region surrounding the conserved histidine and an anti-sense primer designed to the region surrounding the conserved aspartate were used in PCR reactions with either normal ovary or ovarian tumor cDNA as template. In the reaction with ovarian tumor cDNA, a strong product band of the expected size of approximately 180 bp was observed as well as an unexpected PCR product of approximately 300 bp which showed strong expression in some ovarian tumor cDNA's (FIG. 1A). Both of these PCR products were subcloned and sequenced. The sequence of the subclones from the 180 bp band (SEQ ID No. 5) was found to be homologous to the sequence identified in the larger, unexpected band (SEQ ID No. 7) except that the larger band had an additional insert of 133 nucleotides (FIG. 1B). The smaller product of the appropriate size encoded for a protein sequence (SEQ ID No. 6) homologous to other known proteases while the sequence with the insertion (SEQ ID No. 8) encoded for a frame shift from the serine protease catalytic domain and a subsequent premature translational stop codon. TADG-12 variants from four individual tumors were also subcloned and sequenced. It was found that the sequence and insert to be identical. The genomic sequences for these cDNA derived clones were amplified by PCR, examined and found to contain potential AG/GT splice sites that would allow for the variant transcript production (data not shown).

EXAMPLE 10
Northern Blot Analysis of TADG-12 Expression

Figure 2:
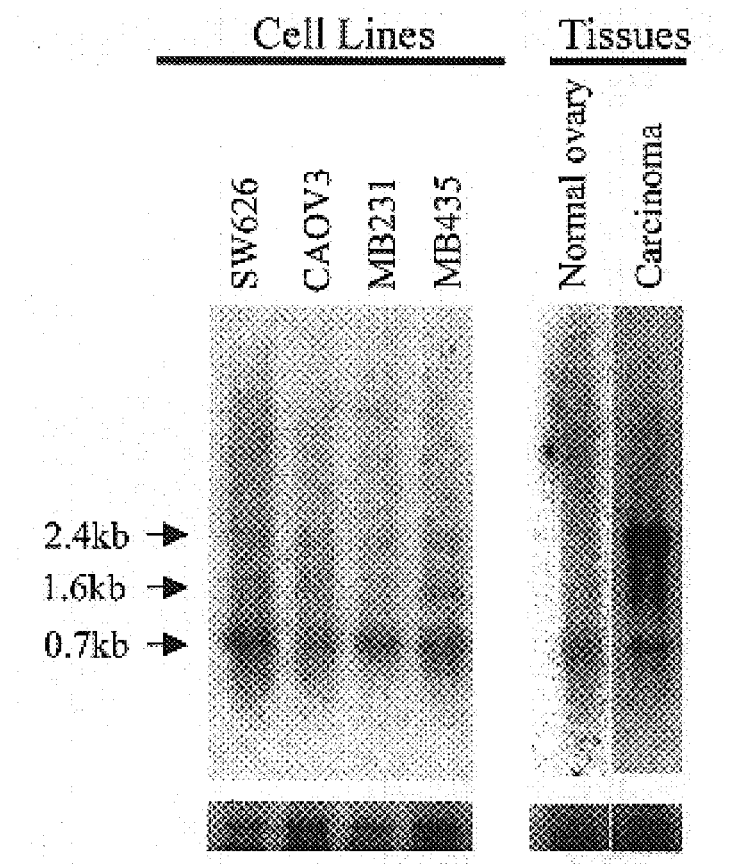
FIG. 2 shows that Northern blot analysis for TADG-12 revealed three transcripts of 2.4, 1.6 and 0.7 kilobases. These transcripts were found at significant levels in ovarian tumors and cancer cell lines, but the transcripts were found only at low levels in normal ovary.
Figure 3:
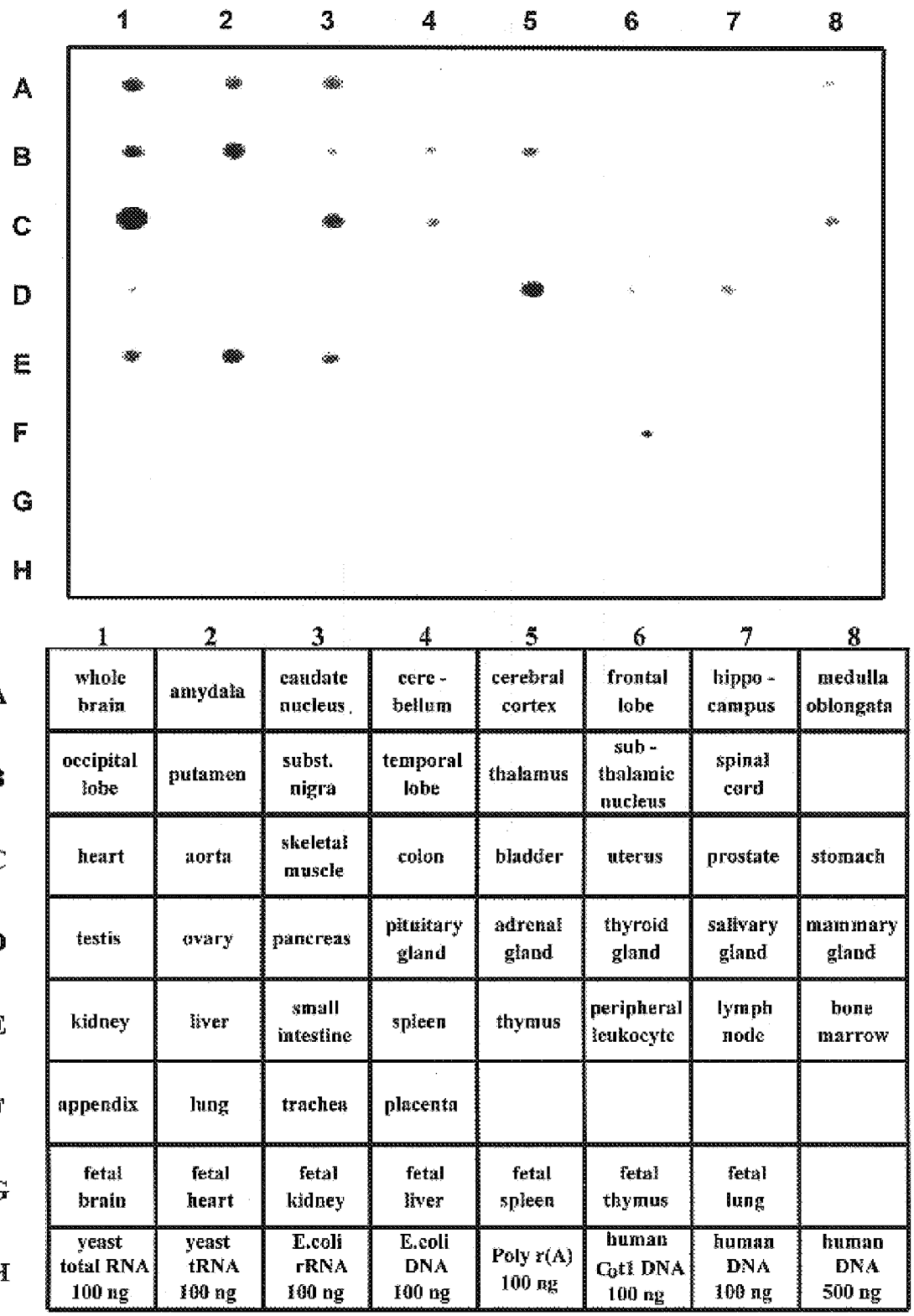
FIG. 3 shows an RNA dot blot (CLONTECH) probed for TADG-12. The transcript was detectable (at background levels) in all 50 of the human tissues represented with the greatest abundance of transcript in the heart. Putamen, amygdala, kidney, liver, small intestine. skeletal muscle, and adrenal gland were also found to have intermediate levels of TADG-12 transcript.

To examine transcript size and tissue distribution, the catalytic domain subclone was randomly labeled and used to probe Northern blots representing normal ovarian tissue, ovarian tumors and the cancer cell lines SW626, CAOV3, HeLa, MD-MBA-435S and MD-MBA-231 (FIG. 2). Three transcripts of 2.4, 1.6 and 0.7 kilobases were observed. In blots of normal and ovary tumor the smallest transcript size 0.7 kb was lowly expressed in normal ovary while all transcripts (2.4, 1.6 and 0.7 kb) were abundantly present in serous carcinoma. In addition, Northern blots representing the normal human tissues spleen, thymus, prostate, testis, ovary, small intestine, colon and peripheral blood leukocyte, and normal human fetal tissues of brain, lung, liver and kidney were examined. The same three transcripts were found to be expressed weakly in all of these tissues (data not shown). A human β-tubulin specific probe was utilized as a control for relative sample loading. In addition, an RNA dot blot was probed representing 50 human tissues and determined that this clone is weakly expressed in all tissues represented (FIG. 3). It was found most prominently in heart, with intermediate levels in putamen, amygdala, kidney, liver, small intestine, skeletal muscle, and adrenal gland.

EXAMPLE 11

Sequencing and Characterization of TADG-12

An ovarian tumor cDNA library constructed in λZAP was screened by standard hybridization techniques using the catalytic domain subclone as a probe. Two clones that overlapped with the probe were identified and sequenced and found to represent 2316 nucleotides. The 97 nucleotides at the 3' end of the transcript including the poly-adenylation signal and the poly (A) tail were identified by homology with clones available in GenBank's EST database. This brought the total size of the transcript to 2413 bases (SEQ ID No. 1, FIG. 4). Subsequent screening of GenBank's Genomic Database revealed that TADG-12 is homologous to a cosmid from chromosome 17. This cosmid has the accession number AC015555.

The identified cDNA includes an open reading frame that would produce a predicted protein of 454 amino acids (SEQ ID No. 2) named Tumor Associated Differentially-Expressed Gene 12 (TADG-12). The sequence has been submitted to the GenBank database and granted the accession #AF201380. Using homology alignment programs, this protein contains several domains including an amino-terminal cytoplasmic domain, a potential Type II transmembrane domain followed by a low-density lipoprotein receptor-like class A domain (LDLR-A), a scavenger receptor cysteine rich domain (SRCR), and an extracellular serine protease domain.

As predicted by the ™Pred program, TADG-12 contains a highly hydrophobic stretch of amino acids that could serve as a potential transmembrane domain, which would retain the amino terminus of the protein within the cytoplasm and expose the ligand binding domains and protease domain to the extracellular space. This general structure is consistent with other known transmembrane proteases including hepsin [17], and TMPRSS2 [18], and TADG-12 is particularly similar in structure to the TMPRSS2 protease.

The LDLR-A domain of TADG-12 is represented by the sequence from amino acid 74 to 108 (SEQ ID No. 13). The LDLR-A domain was originally identified within the LDL Receptor [19] as a series of repeated sequences of approximately 40 amino acids, which contained 6 invariant cysteine residues and highly conserved aspartate and glutamate residues. Since that initial identification, a host of other genes have been identified which contain motifs homologous to this domain [20]. Several proteases have been identified which contain LDLR-A motifs including matriptase, TMPRSS2 and several complement components. A comparison of TADG-12 with other known LDLR-A domains is shown in FIG. 5A. The similarity of these sequences range from 44 to 54% of similar or identical amino acids.

In addition to the LDLR-A domain, TADG-12 contains another extracellular ligand binding domain with homology to the group A SRCR family. This family of protein domains typically is defined by the conservation of 6 cysteine resides within a sequence of approximately 100 amino acids [23]. The SRCR domain of TADG-12 is encoded by amino acids 109 to 206 (SEQ ID No. 17), and this domain was aligned with other SRCR domains and found to have between 36 and 43% similarity (FIG. 5B). However, TADG-12 only has 4 of the 6 conserved cysteine residues. This is similar to the SRCR domain found in the protease TMPRSS2.

The TADG-12 protein also includes a serine protease domain of the trypsin family of proteases. An alignment of the catalytic domain of TADG-12 with other known proteases is shown in FIG. 5C. The similarity among these sequence ranges from 48 to 55%, and TADG-12 is most similar to the serine protease TMPRSS2 which also contains a transmembrane domain, LDLR-A domain and an SRCR domain. There is a conserved amino acid motif (RIVGG) downstream from the SRCR domain that is a potential cleavage/activation site common to many serine proteases of this family [25]. This suggests that TADG-12 is trafficked to the cell surface where the ligand binding domains are capable of interacting with extracellular molecules and the protease domain is potentially activated. TADG-12 also contains conserved cysteine residues (amino acids 208 and 243) which in other proteases form a disulfide bond capable of linking the activated protease to the other extracellular domains.

EXAMPLE 12

Quantitative PCR Characterization of the Alternative Transcript

Figure 6:
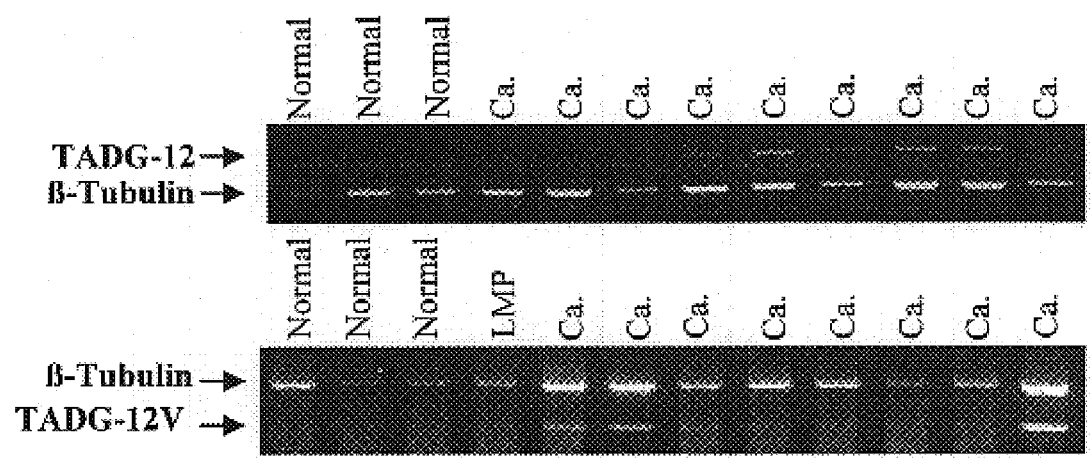
FIG. 6 shows semi-quantitative PCR analysis that was performed for TADG-12 (upper panel) and TADG-12V (lower panel). The amplification of TADG-12 or TADG-12V was performed in parallel with PCR amplification of β-tubulin product as an internal control. The TADG-12 transcript was found to be overexpressed in 41 of 55 carcinomas. The TADG-12V transcript was found to be overexpressed in 8 of 22 carcinomas examined. Note that the samples in the upper panel are not necessarily the same as the samples in the lower panel.

The original TADG-12 subclone was identified as highly expressed in the initial redundant-primer PCR experiment. The TADG-12 variant form (TADG-12V) with the insertion of 133 bp was also easily detected in the initial experiment. To identify the frequency of this expression and whether or not the expression level between normal ovary and ovarian tumors was different, a previously authenticated semi-quantitative PCR technique was employed [16]. The PCR analysis co-amplified a product β-tubulin with either a product specific to TADG-12 or TADG-12V in the presence of a radiolabelled nucleotide. The products were separated by agarose gel electrophoresis and a phosphoimager was used to quantitate the relative abundance of each PCR product. Examples of these PCR amplification products are shown for both TADG-12 and TADG-12V in FIG. 6. Normal expression was defined as the mean ratio of TADG-12 (or TADG-12V) to β-tubulin +/−2SD as examined in normal ovarian samples. For tumor samples, overexpression was defined as >2SD from the normal TADG-12/β-tubulin or TADG-12V/β-tubulin ratio. The results are summarized in Table 1 and Table 2. TADG-12 was found to be overexpressed in 41 of 55 carcinomas examined while the variant form was present at aberrantly high levels in 8 of 22 carcinomas. As determined by the student's test, these differences were statistically significant (p<0.05).

TABLE 1

Frequency of Overexpression of TADG-12 in Ovarian Carcinoma

| Histology Type | TADG-12 (%) |
| --- | --- |
| Normal | 0/16 (0%) |
| LMP-Serous | 3/6 (50%) |
| LMP-Mucinous | 0/4 (0%) |
| Serous Carcinoma | 23/29 (79%) |
| Mucinous Carcinoma | 7/12 (58%) |
| Endometrioid Carcinoma | 8/8 (100%) |
| Clear Cell Carcinoma | 3/6 (50%) |
| Benign Tumors | 3/4 (75%) |

Overexpression = more than two standard deviations above the mean for normal ovary
LMP = low malignant potential tumor

TABLE 2

Frequency of Overexpression of TADG-12V in Ovarian Carcinoma

| Histology Type | TADG-12V (%) |
| --- | --- |
| Normal | 0/10 (0%) |
| LMP-Serous | 0/5 (0%) |

TABLE 2-continued

Frequency of Overexpression of TADG-12V in Ovarian Carcinoma

| Histology Type | TADG-12V (%) |
|---|---|
| LMP-Mucinous | 0/3 (0%) |
| Serous Carcinoma | 4/14 (29%) |
| Mucinous Carcinoma | 3/5 (60%) |
| Endometrioid Carcinoma | 1/3 (33%) |
| Clear Cell Carcinoma | N/D |

Overexpression = more than two standard deviations above the mean for normal ovary
LMP = low malignant potential tumor

EXAMPLE 13
Immunohistochemical Analysis of TADG-12 in Ovarian Tumor Cells

Figure 7A:
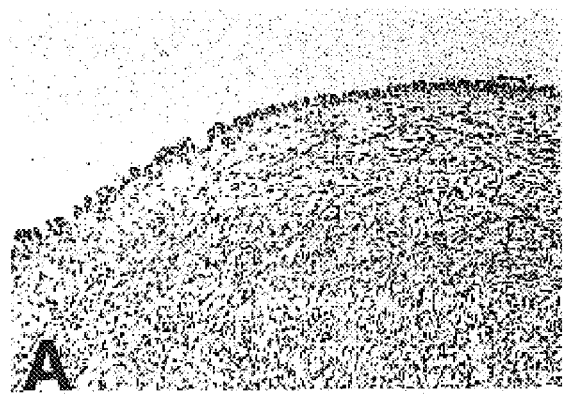
FIG. 7 shows immunohistochemical staining of normal ovary and ovarian tumors which were performed using a polyclonal rabbit antibody developed to a TADG-12 specific peptide. No significant staining was detected in normal ovary (FIG. 7A). Strong positive staining was observed in 22 of 29 carcinomas examined.
FIGS. 7B and 7C represent a serous and mucinous carcinoma, respectively. Both show diffuse staining throughout the cytoplasm of tumor cells while stromal cells remain relatively sustained.
Figure 7B:
Figure 7C:
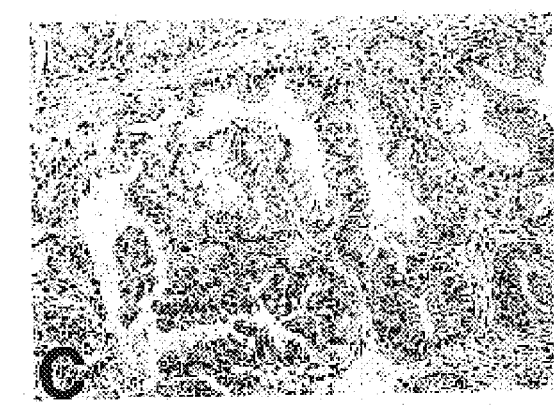

In order to examine the TADG-12 protein, polyclonal rabbit anti-sera a peptide located in the carboxy-terminal amino acid sequence was developed. These antibodies were used to examine the expression level of the TADG-12 protein and its localization within normal ovary and ovarian tumor cells by immuno-localization. No staining was observed in normal ovarian tissues (FIG. 7A) while significant staining was observed in 22 of 29 tumors studied. Representative tumor samples are shown in FIGS. 7B and 7C. It should be noted that TADG-12 is found in a diffuse pattern throughout the cytoplasm indicative of a protein in a trafficking pathway. TADG-12 is also found at the cell surface in these tumor samples as expected. It should be noted that the antibody developed and used for immunohistochemical analysis would not detect the TADG-12V truncated protein.

The results of the immunohistochemical staining are summarized in Table 3. 22 of 29 ovarian tumors showed positive staining of TADG-12, whereas normal ovarian surface epithelium showed no expression of the TADG-12 antigen. 8 of 10 serous adenocarcinomas, 8 of 8 mucinous adenocarcinomas, 1 of 2 clear cell carcinomas, and 4 of 6 endometroid carcinomas showed positive staining.

TABLE 3

| Case | Stage | Histology | Grade | LN* | TADG12 | Prognosis |
|---|---|---|---|---|---|---|
| 1 | | Normal ovary | | | 0− | |
| 2 | | Normal ovary | | | 0− | |
| 3 | | Normal ovary | | | 0− | |
| 4 | | Mucinous B | | ND | 0− | Alive |
| 5 | | Mucinous B | | ND | 1+ | Alive |
| 6 | 1a | Serous LMP | G1 | ND | 1+ | Alive |
| 7 | 1a | Mucinous LMP | G1 | ND | 1+ | Alive |
| 8 | 1a | Mucinous CA | G1 | ND | 1+ | Alive |
| 9 | 1a | Mucinous CA | G2 | ND | 1+ | Alive |
| 10 | 1a | Endometrioid CA | G1 | ND | 0− | Alive |
| 11 | 1c | Serous CA | G1 | N | 1+ | Alive |
| 12 | 1c | Mucinous CA | G1 | N | 1+ | Alive |
| 13 | 1c | Mucinous CA | G1 | N | 2+ | Alive |
| 14 | 1c | Clear cell CA | G2 | N | 0− | Alive |
| 15 | 1c | Clear cell CA | G2 | N | 0− | Alive |
| 16 | 2c | Serous CA | G3 | N | 2+ | Alive |
| 17 | 3a | Mucinous CA | G2 | N | 2+ | Alive |
| 18 | 3b | Serous CA | G1 | ND | 1+ | Alive |
| 19 | 3c | Serous CA | G1 | N | 0− | Dead |
| 20 | 3c | Serous CA | G3 | P | 1+ | Alive |
| 21 | 3c | Serous CA | G2 | P | 2+ | Alive |
| 22 | 3c | Serous CA | G1 | P | 2+ | Unknown |
| 23 | 3c | Serous CA | G3 | ND | 2+ | Alive |
| 24 | 3c | Serous CA | G2 | N | 0− | Dead |
| 25 | 3c | Mucinous CA | G1 | P | 2+ | Dead |
| 26 | 3c | Mucinous CA | G2 | ND | 1+ | Unknown |
| 27 | 3c | Mucinous CA | G2 | N | 1+ | Alive |
| 28 | 3c | Endometrioid CA | G1 | P | 1+ | Dead |
| 29 | 3c | Endometrioid CA | G2 | N | 0− | Alive |
| 30 | 3c | Endometrioid CA | G2 | P | 1+ | Dead |
| 31 | 3c | Endometrioid CA | G3 | P | 1+ | Alive |
| 32 | 3c | Clear Cell CA | G3 | P | 2+ | Dead |

LN* = Lymph Node: B = Benign; N = Negative; P = Positive;
ND = Not Done

EXAMPLE 14
Peptide Ranking

For vaccine or immune stimulation, individual 9-mers to 11-mers of the TADG-12 protein were examined to rank the binding of individual peptides to the top 8 haplotypes in the general population [Parker et al., (1994)]. The computer program used for this analysis can be found at <http://www-bimas.dert.nih.gov/molbio/hla_bind/>. Table 4 shows the peptide ranking based upon the predicted half-life of each peptide's binding to a particular HLA allele. A larger half-life indicates a stronger association with that peptide and the particular HLA molecule. The TADG-12 peptides that strongly bind to an HLA allele are putative immunogens, and are used to innoculate an individual against TADG-12.

TABLE 4

TADG-12 peptide ranking

| HLA Type & Ranking | Start | Peptide | Predicted Dissociation½ | SEQ ID No. |
|---|---|---|---|---|
| HLA A0201 | | | | |
| 1 | 40 | ILSLLPFEV | 685.783 | 35 |
| 2 | 144 | AQLGFPSYV | 545.316 | 36 |
| 3 | 225 | LLSQWPWQA | 63.342 | 37 |
| 4 | 252 | WIITAAHCV | 43.992 | 38 |
| 5 | 356 | VLNHAAVPL | 36.316 | 39 |
| 6 | 176 | LLPDDKVTA | 34.627 | 40 |
| 7 | 13 | FSFRSLFGL | 31.661 | 41 |
| 8 | 151 | YVSSDNLRV | 27.995 | 42 |
| 9 | 436 | RVTSFLDWI | 21.502 | 43 |
| 10 | 234 | SLQFQGYHL | 21.362 | 44 |
| 11 | 181 | KVTALHHSV | 21.300 | 45 |
| 12 | 183 | TALHHSVYV | 19.658 | 46 |
| 13 | 411 | RLWKLVGAT | 18.494 | 47 |
| 14 | 60 | LILALAIGL | 18.476 | 48 |
| 15 | 227 | SQWPWQASL | 17.977 | 49 |
| 16 | 301 | RLGNDIALM | 11.426 | 50 |
| 17 | 307 | ALMKLAGPL | 10.275 | 51 |
| 18 | 262 | DLYLPKSWT | 9.837 | 52 |
| 19 | 416 | LVGATSFGI | 9.001 | 53 |
| 20 | 54 | SLGIIALIL | 8.759 | 54 |
| HLA A0205 | | | | |
| 1 | 218 | IVGGNMSLL | 47.600 | 55 |
| 2 | 60 | LILALAIGL | 35.700 | 48 |
| 3 | 35 | AVAAQILSL | 28.000 | 56 |
| 4 | 307 | ALMKLAGPL | 21.000 | 51 |
| 5 | 271 | IQVGLVSLL | 19.040 | 57 |
| 6 | 397 | CQGDSGGPL | 16.800 | 58 |
| 7 | 227 | SQWPWQASL | 16.800 | 49 |
| 8 | 270 | TIQVGLVSL | 14.000 | 59 |
| 9 | 56 | GIIALILAL | 14.000 | 60 |
| 10 | 110 | RVGGQNAVL | 14.000 | 61 |
| 11 | 181 | KVTALHHSV | 12.000 | 45 |
| 12 | 151 | YVSSDNLRV | 12.000 | 42 |
| 13 | 356 | VLNHAAVPL | 11.900 | 39 |
| 14 | 144 | AQLGFPSYV | 9.600 | 36 |
| 15 | 13 | FSFRSLFGL | 7.560 | 41 |

TABLE 4-continued

TADG-12 peptide ranking

| HLA Type & Ranking | Start | Peptide | Predicted Dissociation½ | SEQ ID No. |
|---|---|---|---|---|
| 16 | 54 | SLGIIALIL | 7.000 | 54 |
| 17 | 234 | SLQFQGYHL | 7.000 | 44 |
| 18 | 217 | RIVGGNMSL | 7.000 | 62 |
| 19 | 411 | RLWKLVGAT | 6.000 | 47 |
| 20 | 252 | WIITAAHCV | 6.000 | 38 |
| HLA A1 | | | | |
| 1 | 130 | CSDDWKGHY | 37.500 | 63 |
| 2 | 8 | AVEAPFSFR | 9.000 | 64 |
| 3 | 328 | NSEENFPDG | 2.700 | 65 |
| 4 | 3 | ENDPPAVEA | 2.500 | 66 |
| 5 | 98 | DCKDGEDEY | 2.500 | 67 |
| 6 | 346 | ATEDGGDAS | 2.250 | 68 |
| 7 | 360 | AAVPLISNK | 2.000 | 69 |
| 8 | 153 | SSDNLRVSS | 1.500 | 70 |
| 9 | 182 | VTALHHSVY | 1.250 | 71 |
| 10 | 143 | CAQLGFPSY | 1.000 | 72 |
| 11 | 259 | CVYDLYLPK | 1.000 | 73 |
| 12 | 369 | ICNHRDVYG | 1.000 | 74 |
| 13 | 278 | LLDNPAPSH | 1.000 | 75 |
| 14 | 426 | CAEVNKPGV | 1.000 | 76 |
| 15 | 32 | DADAVAAQI | 1.000 | 77 |
| 16 | 406 | VCQERRLWK | 1.000 | 78 |
| 17 | 329 | SEENFPDGK | 0.900 | 79 |
| 18 | 303 | GNDIALMKL | 0.625 | 80 |
| 19 | 127 | KTMCSDDWK | 0.500 | 81 |
| 20 | 440 | FLDWIHEQM | 0.500 | 82 |
| HLA A24 | | | | |
| 1 | 433 | VYTRVTSFL | 280.000 | 83 |
| 2 | 263 | LYLPKSWTI | 90.000 | 84 |
| 3 | 169 | EFVSIDHLL | 42.000 | 85 |
| 4 | 217 | RIVGGNMSL | 12.000 | 62 |
| 5 | 296 | KYKPKRLGN | 12.000 | 86 |
| 6 | 16 | RSLFGLDDL | 12.000 | 87 |
| 7 | 267 | KSWTIQVGL | 11.200 | 88 |
| 8 | 81 | RSSFKCIEL | 8.800 | 89 |
| 9 | 375 | VYGGIISPS | 8.000 | 90 |
| 10 | 110 | RVGGQNAVL | 8.000 | 91 |
| 11 | 189 | VYVREGCAS | 7.500 | 92 |
| 12 | 60 | LILALAIGL | 7.200 | 48 |
| 13 | 165 | QFREEFVSI | 7.200 | 93 |
| 14 | 271 | IQVGLVSLL | 7.200 | 57 |
| 15 | 56 | GIIALILAL | 7.200 | 60 |
| 16 | 10 | EAPFSFRSL | 7.200 | 94 |
| 17 | 307 | ALMKLAGPL | 7.200 | 51 |
| 18 | 407 | CQERRLWKL | 6.600 | 95 |
| 19 | 356 | VLNHAAVPL | 6.000 | 39 |
| 20 | 381 | SPSMLCAGY | 6.000 | 96 |
| HLA B7 | | | | |
| 1 | 375 | VYGGIISPS | 200.000 | 97 |
| 2 | 381 | SPSMLCAGY | 80.000 | 98 |
| 3 | 362 | VPLISNKIC | 80.000 | 99 |
| 4 | 35 | AVAAQILSL | 60.000 | 56 |
| 5 | 373 | RDVYGGIIS | 40.000 | 100 |
| 6 | 307 | ALMKLAGPL | 36.000 | 51 |
| 7 | 283 | APSHLVEKI | 24.000 | 101 |
| 8 | 177 | LPDDKVTAL | 24.000 | 102 |
| 9 | 47 | EVFSQSSSL | 20.000 | 103 |
| 10 | 110 | RVGGQNAVL | 20.000 | 91 |
| 11 | 218 | IVGGNMSLL | 20.000 | 55 |
| 12 | 36 | VAAQILSLL | 12.000 | 104 |
| 13 | 255 | TAAHCVYDL | 12.000 | 105 |
| 14 | 10 | EAPFSFRSL | 12.000 | 94 |
| 15 | 138 | YANVACAQL | 12.000 | 106 |
| 16 | 195 | CASGHVVTL | 12.000 | 107 |
| 17 | 215 | SSRIVGGNM | 10.000 | 108 |
| 18 | 298 | KPKRLGNDI | 8.000 | 109 |
| 19 | 313 | GPLTFNEMI | 8.000 | 110 |
| 20 | 108 | CVRVGGQNA | 5.000 | 111 |
| HLA B8 | | | | |
| 1 | 294 | HSKYKPKRL | 80.000 | 112 |
| 2 | 373 | RDVYGGIIS | 16.000 | 100 |
| 3 | 177 | LPDDKVTAL | 4.800 | 102 |
| 4 | 265 | LPKSWTIQV | 2.400 | 113 |
| 5 | 88 | ELITRCDGV | 2.400 | 114 |
| 6 | 298 | KPKRLGNDI | 2.000 | 109 |
| 7 | 81 | RSSFKCIEL | 2.000 | 89 |
| 8 | 375 | VYGGIISPS | 2.000 | 97 |
| 9 | 79 | RCRSSFKCI | 2.000 | 115 |
| 10 | 10 | EAPFSFRSL | 1.600 | 94 |
| 11 | 215 | SSRIVGGNM | 1.000 | 108 |
| 12 | 36 | VAAQILSLL | 0.800 | 104 |
| 13 | 255 | TAAHCVYDL | 0.800 | 116 |
| 14 | 381 | SPSMLCAGY | 0.800 | 98 |
| 15 | 195 | CASGHVVTL | 0.800 | 107 |
| 16 | 362 | VPLISNKIC | 0.800 | 99 |
| 17 | 138 | YANVACAQL | 0.800 | 106 |
| 18 | 207 | ACGHRRGYS | 0.400 | 117 |
| 19 | 154 | SDNLRVSSL | 0.400 | 118 |
| 20 | 47 | EVFSQSSSL | 0.400 | 103 |
| HLA B2702 | | | | |
| 1 | 300 | KRLGNDIAL | 180.000 | 119 |
| 2 | 435 | TRVTSFLDW | 100.000 | 120 |
| 3 | 376 | YGGIISPSM | 100.000 | 121 |
| 4 | 410 | RRLWKLVGA | 60.000 | 122 |
| 5 | 210 | HRRGYSSRI | 60.000 | 123 |
| 6 | 227 | SQWPWQASL | 30.000 | 49 |
| 7 | 109 | VRVGGQNAV | 20.000 | 124 |
| 8 | 191 | VREGCASGH | 20.000 | 125 |
| 9 | 78 | YRCRSSFKC | 20.000 | 126 |
| 10 | 113 | GQNAVLQVF | 20.000 | 127 |
| 11 | 91 | TRCDGVSDC | 20.000 | 128 |
| 12 | 38 | AQILSLLPF | 20.000 | 129 |
| 13 | 211 | RRGYSSRIV | 18.000 | 130 |
| 14 | 216 | SRIVGGNMS | 10.000 | 131 |
| 15 | 118 | LQVFTAASW | 10.000 | 132 |
| 16 | 370 | CNHRDVYGG | 10.000 | 133 |
| 17 | 393 | GVDSCQGDS | 10.000 | 134 |
| 18 | 235 | LQFQGYHLC | 10.000 | 135 |
| 19 | 271 | IQVGLVSLL | 6.000 | 57 |
| 20 | 408 | CQERRLWKL | 6.000 | 95 |
| HLA B4403 | | | | |
| 1 | 427 | AEVNKPGVY | 90.000 | 136 |
| 2 | 162 | LEGQFREEF | 40.000 | 137 |
| 3 | 9 | VEAPFSFRS | 24.000 | 138 |
| 4 | 318 | NEMIQPVCL | 12.000 | 139 |
| 5 | 256 | AAHCVYDLY | 9.000 | 140 |
| 6 | 98 | DCKDGEDEY | 9.000 | 67 |
| 7 | 46 | FEVFSQSSS | 8.000 | 141 |
| 8 | 38 | AQILSLLPF | 7.500 | 129 |
| 9 | 64 | LAIGLGIHF | 7.500 | 142 |
| 10 | 192 | REGCASGHV | 6.000 | 143 |
| 11 | 330 | EENFPDGKV | 6.000 | 144 |
| 12 | 182 | VTALHHSVY | 6.000 | 145 |
| 13 | 408 | QERRLWKLV | 6.000 | 146 |
| 14 | 206 | TACGHRRGY | 4.500 | 147 |
| 15 | 5 | DPPAVEAPF | 4.500 | 148 |
| 16 | 261 | YDLYLPKSW | 4.500 | 149 |
| 17 | 33 | ADAVAAQIL | 4.500 | 150 |
| 18 | 168 | EEFVSIDHL | 4.000 | 151 |
| 19 | 304 | NDIALMKLA | 3.750 | 152 |
| 20 | 104 | DEYRCVRVG | 3.600 | 153 |

Conclusion

In this study, a serine protease was identified by means of a PCR based strategy. By Northern blot, the largest transcript for this gene is approximately 2.4 kb, and it is found to be expressed at high levels in ovarian tumors while found at minimal levels in all other tissues examined. The full-length cDNA encoding a novel multi-domain, cell-surface serine protease was cloned, named TADG-12. The 454 amino acid protein contains a cytoplasmic domain, a type II transmembrane domain, an LDLR-A domain, an SRCR domain and a serine protease domain. Using a semi-quantitative PCR analysis, it was shown that TADG-12 is overexpressed in a majority of tumors studied. Immunohistochemical staining corroborates that in some cases this protein is localized to the cell-surface of tumor cells and this suggests that TADG-12 has some extracellular proteolytic functions. Interestingly, TADG-12 also has a variant splicing form that is present in 35% of the tumors studied. This variant mRNA would lead to a truncated protein that may provide a unique peptide sequence on the surface of tumor cells.

This protein contains two extracellular domains which might confer unusual properties to this multidomain molecule. Although the precise role of LDLR-A function with regard to proteases remains unclear, this domain certainly has the capacity to bind calcium and other positively charged ligands [21,22]. This may play an important role in the regulation of the protease or subsequent internalization of the molecule. The SRCR domain was originally identified within the macrophage scavenger receptor and functionally described to bind lipoproteins. Not only are SRCR domains capable of binding lipoproteins, but they may also bind to molecules as diverse as polynucleotides [23]. More recent studies have identified members of this domain family in proteins with functions that vary from proteases to cell adhesion molecules involved in maturation of the immune system [24]. In addition, TADG-12, like TMPRSS2 has only four of six cysteine residues conserved within its SRCR domain. This difference may allow for different structural features of these domains that confer unusual ligand binding properties. At this time, only the function of the CD6 encoded SRCR is well documented. In the case of CD6, the SRCR domain binds to the cell adhesion molecule ALCAM [23]. This mediation of cell adhesion is a useful starting point for future research on newly identified SRCR domains, however, the possibility of multiple functions for this domain can not be overlooked. SRCR domains are certainly capable of cell adhesion type interactions, but their capacity to bind other types of ligands should be considered.

Figure 8:
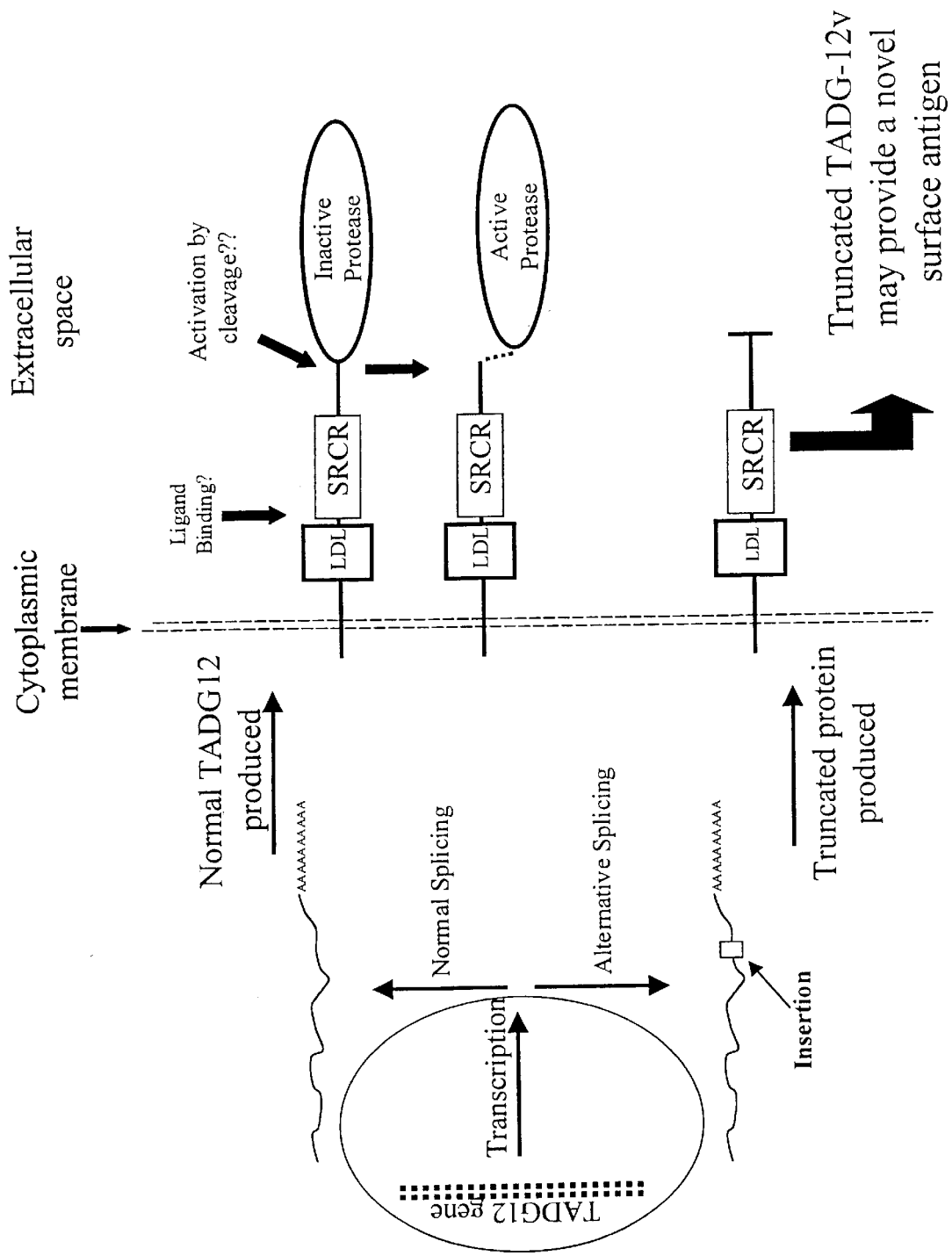
FIG. 8 is a model to demonstrate the progression of TADG-12 within a cellular context. In normal circumstances, the TADG-12 transcript is appropriately spliced and the resulting protein is capable of being expressed at the cell surface where the protease may be cleaved to an active form. The role of the remaining ligand binding domains has not yet been determined, but one can envision their potential to bind other molecules for activation, internalization or both. The TADG-12V transcript, which occurs in some tumors, may be the result of mutation and/or poor mRNA processing may be capable of producing a truncated form of TADG-12 that does not have a functional protease domain. In addition, this truncated product may present a novel epitope at the surface of tumor cells.

At this time, the precise role of TADG-12 remains unclear. Substrates have not been identified for the protease domain, nor have ligands been identified for the extracellular LDLR-A and SRCR domains. FIG. 8 presents a working model of TADG-12 with the information disclosed with the present invention. Two transcripts are produced which lead to the production of either TADG-12 or the truncated TADG-12V proteins. Either of these proteins is potentially targeted to the cell surface. TADG-12 is capable of becoming an activated serine protease while TADG-12V is a truncated protein product that if at the cell surface may represent a tumor specific epitope.

The problem with treatment of ovarian cancer today remains the inability to diagnose the disease at an early stage. Identifying genes that are expressed early in the disease process such as proteases that are essential for tumor cell growth [26] is an important step toward improving treatment. With this knowledge, it may be possible to design assays to detect the highly expressed genes such as the TADG-12 protease described here or previously described proteases to diagnose these cancers at an earlier stage. Panels of markers may also provide prognostic information and could lead to therapeutic strategies for individual patients. Alternatively, inhibition of enzymes such as proteases may be an effective means for slowing progression of ovarian cancer and improving the quality of patient life. Other features of TADG-12 and TADG-12V must be considered important to future research too. The extracellular ligand binding domains are natural targets for drug delivery systems. The aberrant peptide associated with the TADG-12V protein may provide an excellent target drug delivery or for immune stimulation.

The following references were cited herein.

1. Duffy. M. J. Clin. Exp. Metastasis, 10: 145–155, 1992.
2. Monsky, W. L., et al., Cancer Res., 53: 3159–3164, 1993.
3. Powell, W. C., et al., Cancer Res., 53: 417–422, 1993.
4. Neurath, H. The Diversity of Proteolytic Enzymes, In: R. J. Beynon and J. S. Bond (eds.), pp. 1–13, Proteolytic enzymes, Oxford: IRL Press. 1989.
5. Liotta, L. A., et al., Cell, 64: 327–336, 1991.
6. Tryggvason, K., et al., Biochem. Biophys. Acta., 907: 191–217, 1987.
7. McCormack, R. T., et al., Urology, 45:729–744, 1995.
8. Landis, S. H., et al., CA Cancer J. Clin., 48: 6–29, 1998.
9. Tanimoto, H., et al., Cancer Res., 57: 2884–2887, 1997.
10. Tanimoto, H., et al., Cancer, 86: 2074–2082, 1999.
11. Underwood, L. J., et al., Cancer Res., 59:4435–4439, 1999.
12. Tanimoto, H., Underwood, L. J., Shigemasa, K., Parmley T. H., and O'Brien, T. J. Increased Expression of Protease M in Ovarian Tumors. Tumor Biology, In Press, 2000.
13. Tanimoto, H., et al., Proc. Of the Amer. Assoc. for Canc. Research 39:648. 1998.
14. Tanimoto, H., et al., Tumor Biology, 20: 88–98, 1999.
15. Maniatis, T., Fritsch, E. F. & Sambrook, J. Molecular Cloning, p. 309–361 Cold Spring Harbor Laboratory, New York, 1982.
16. Shigemasa, K., et al., J. Soc. Gynecol. Invest., 4:95–102, 1997.
17. Leytus S. P., et al., Biochemistry, 27: 1067–1074, 1988.
18. Paoloni-Giacobino, A., et al., Genomics, 44: 309–320, 1997.
19. Sudhof, T. C., et al., Science, 228: 815–822, 1985.
20. Daly, N. L., et al., Proc. Natl. Acad. Sci. USA 92: 6334–6338, 1995.
21. Mahley, R. W., Science 240: 622–630, 1988.
22. Van Driel, I. R., et al., J. Biol. Chem. 262: 17443–17449, 1987.
23. Freeman, M., et al., Proc. Natl. Acad. Sci. USA 87: 8810–8814, 1990.
24. Aruffo, A., et al., Immunology Today 18(10): 498–504, 1997.
25. Rawlings, N. D., and Barrett, A. J., Methods Enzymology 244: 19–61, 1994.
26. Torres-Rosado, A., et al., Proc. Natl. Acad. Sci. USA, 90: 7181–7185. 1993.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for diagnosing cancer in an individual comprising the steps of:
    (a) obtaining a biological sample from said individual;
    (b) detecting a TADG-12 protein in said sample, wherein a TADG-12 protein is selected from the group consisting of SEQ ID NO:2, SEQ ID NO:4 and SEQ ID NO:8, and wherein the presence of said TADG-12 protein in said sample is indicative of the presence of a cancer in said individual, and wherein the absence of said TADG-12 protein in said sample is indicative of the absence of a cancer in said individual.

2. The method of claim 1, wherein said biological sample is selected from the group consisting of blood, urine, saliva, tears, interstitial fluid, ascites fluid, tumor tissue biopsy and circulating tumor cells.

3. The method of claim 1, wherein said detection of a TADG-12 protein is by means selected from the group consisting of Western blot, dot blot, ELIZA sandwich assay, radioimmunoassay and flow cytometry.

4. The method of claim 1, wherein said cancer is selected from the group consisting of ovarian caner, breast cancer, lung cancer, colon caner, prostate cancer and other cancers in which TADG-12 is overexpressed.

5. A method for detecting malignant hyperplasia in a biological sample, comprising the steps of:
(a) isolating protein from said sample;
(b) detecting a TADG-12 protein in said sample, wherein a TADG-12 protein is selected from the group consisting of SEQ ID NO:2, SEQ ID NO:4 and SEQ ID NO:8, and wherein the presence of said TADG-12 protein in said sample is indicative of the presence of malignant hyperplasia, and wherein the absence of said TADG-12 protein in said sample is indicative of the absence of malignant hyperplasia.

6. The method of claim 5, wherein said detection is by immunoaffinity to an antibody, wherein said antibody is directed against a TADG-12 protein.

7. The method of claim 5, wherein said biological sample is selected from the group consisting of blood, urine, saliva, tears, interstitial fluid, ascites fluid, tumor tissue biopsy and circulating tumor cells.

* * * * *